United States Patent
Ishizuka et al.

(10) Patent No.: US 11,337,597 B2
(45) Date of Patent: May 24, 2022

(54) IMAGING MODULE AND METHOD OF MANUFACTURING THE SAME

(71) Applicant: Fujikura Ltd., Tokyo (JP)

(72) Inventors: Takeshi Ishizuka, Sakura (JP); Kenichi Ishibashi, Sakura (JP); Hideaki Usuda, Tokyo (JP)

(73) Assignee: FUJIKURA LTD., Tokyo (JP)

( * ) Notice: Subject to any disclaimer, the term of this patent is extended or adjusted under 35 U.S.C. 154(b) by 140 days.

(21) Appl. No.: 16/037,125

(22) Filed: Jul. 17, 2018

(65) Prior Publication Data
US 2019/0021581 A1    Jan. 24, 2019

(30) Foreign Application Priority Data

Jul. 19, 2017  (JP) .............................. JP2017-140297

(51) Int. Cl.
    *A61B 1/05*     (2006.01)
    *H05K 3/34*     (2006.01)
    *H04N 5/225*    (2006.01)

(52) U.S. Cl.
    CPC ........... *A61B 1/051* (2013.01); *H04N 5/2253* (2013.01); *H05K 3/3405* (2013.01);
    (Continued)

(58) Field of Classification Search
    CPC ..... H01L 2224/291; H01L 2224/00014; H01L 2224/02371; H01L 2224/32225;
    (Continued)

(56) References Cited

U.S. PATENT DOCUMENTS

| 5,795,818 A | * | 8/1998 | Marrs ..................... H01L 24/81 438/612 |
| 6,567,115 B1 | | 5/2003 | Miyashita et al. |

(Continued)

FOREIGN PATENT DOCUMENTS

| EP | 2 683 225 A1 | 1/2014 |
| JP | S60-039276 U | 3/1985 |

(Continued)

OTHER PUBLICATIONS

Office Action dated Mar. 12, 2019, issued in counterpart JP application No. 2017-140297, with English translation. (6 pages).
(Continued)

*Primary Examiner* — Kathleen V Nguyen
(74) *Attorney, Agent, or Firm* — Westerman, Hattori, Daniels & Adrian, LLP

(57) ABSTRACT

An imaging module of the invention includes: an imaging element; and a substrate positioned on a rear surface opposite to an imaging surface of the imaging element and provided to extend from the rear surface to a side opposite to the imaging surface. An electrode pad provided on the rear surface of the imaging element and a front end portion of an electrode pad provided on a main surface of the substrate at a position close to the imaging element are electrically connected via a conductive connecting material portion. A notch portion recessed from a distal end of the front end portion is formed at the front end portion of the electrode pad of the substrate.

12 Claims, 13 Drawing Sheets

(52) U.S. Cl.
CPC .............. *H01L 2224/02371* (2013.01); *H01L 2224/291* (2013.01); *H01L 2224/32225* (2013.01); *H05K 2201/09181* (2013.01); *H05K 2201/10121* (2013.01); *H05K 2201/10356* (2013.01)

(58) Field of Classification Search
CPC .............. A61B 1/051; H04N 5/2253; H05K 2201/09181; H05K 2201/101221; H05K 2201/10356
USPC .......................................................... 348/76
See application file for complete search history.

(56) References Cited

U.S. PATENT DOCUMENTS

| | | | | |
|---|---|---|---|---|
| 2006/0118330 | A1* | 6/2006 | Ooyabu | H05K 3/363 174/261 |
| 2009/0044969 | A1* | 2/2009 | Ishii | H05K 3/363 174/255 |
| 2011/0249106 | A1 | 10/2011 | Makino et al. | |
| 2016/0072989 | A1* | 3/2016 | Kennedy, II | A61B 1/051 348/76 |
| 2018/0249896 | A1 | 9/2018 | Mikami | |

FOREIGN PATENT DOCUMENTS

| | | | |
|---|---|---|---|
| JP | 2924113 | * | 3/1992 |
| JP | 2924113 | B2 | 7/1999 |
| JP | 2000-199863 | A | 7/2000 |
| JP | 2000-232957 | A | 8/2000 |
| JP | 2001-043739 | A | 2/2001 |
| JP | 2006-014906 | A | 1/2006 |
| JP | 2011-217887 | A | 11/2011 |
| JP | 5926890 | B2 | 5/2016 |
| TW | M353600 | * | 3/2009 |
| TW | M353600 | U1 | 3/2009 |
| WO | 2017/081720 | A1 | 5/2017 |

OTHER PUBLICATIONS

Extended European Search Report dated Oct. 31, 2018, issued in counterpart European Application No. 18183517.4. (7 pages).

* cited by examiner

FIG. 1A
FIG. 1B
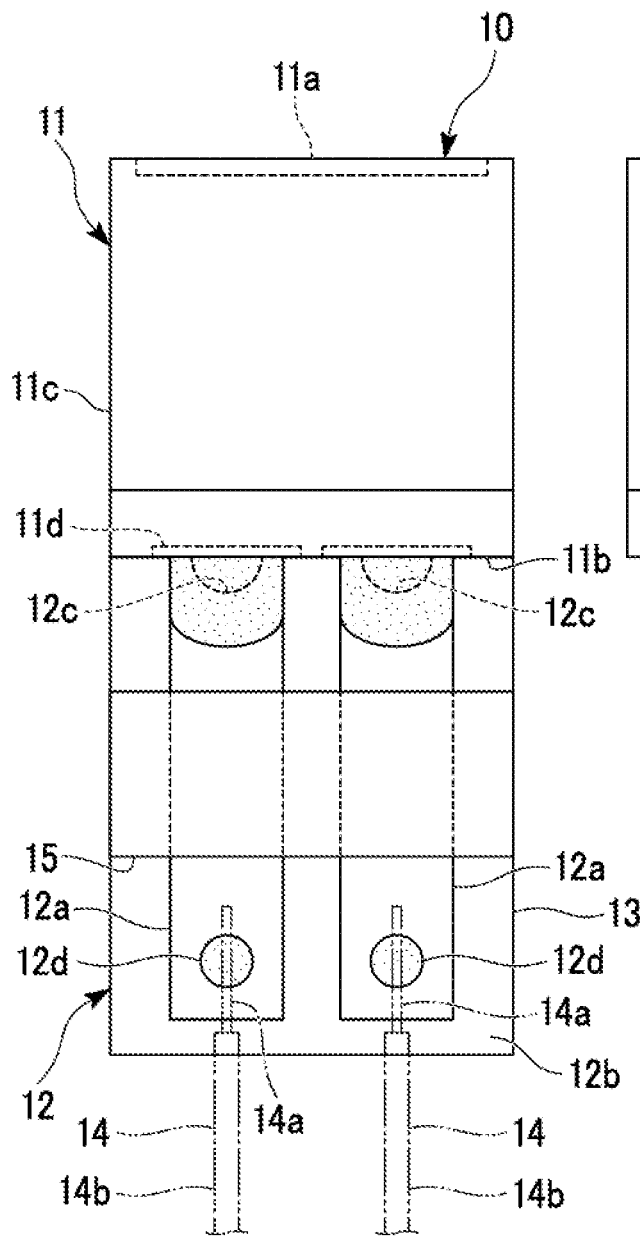
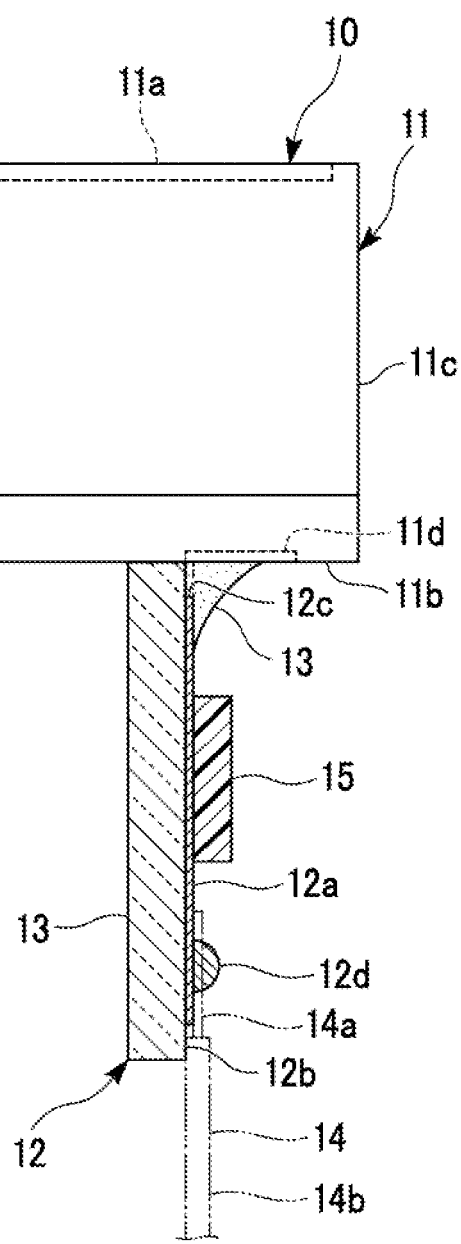
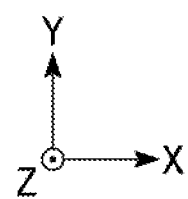
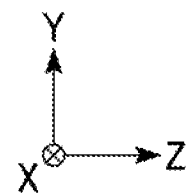

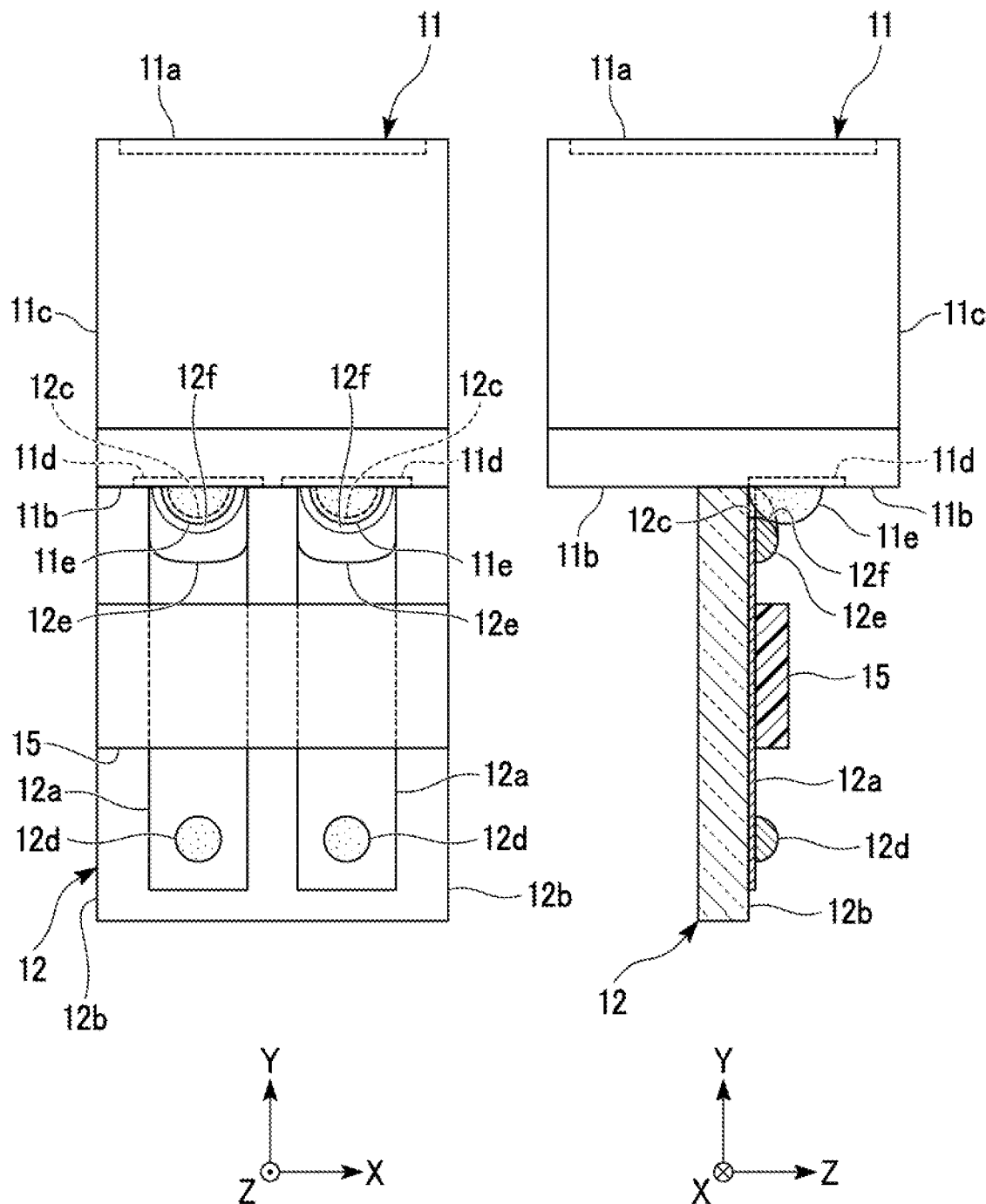

FIG. 4A
FIG. 4B
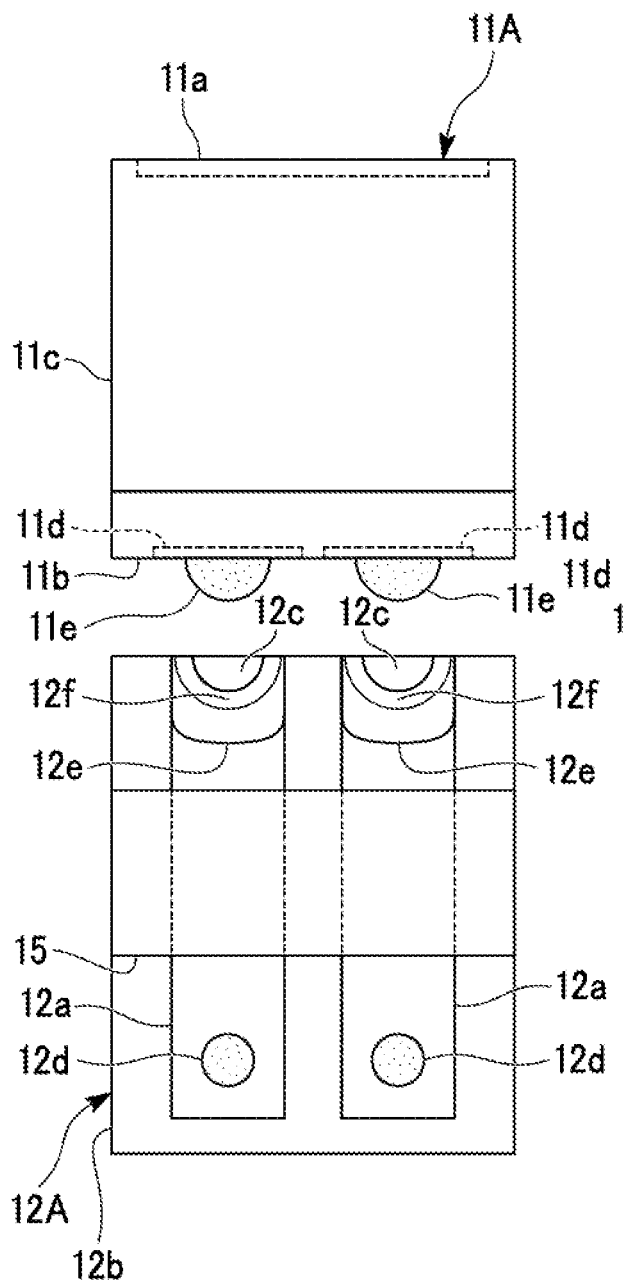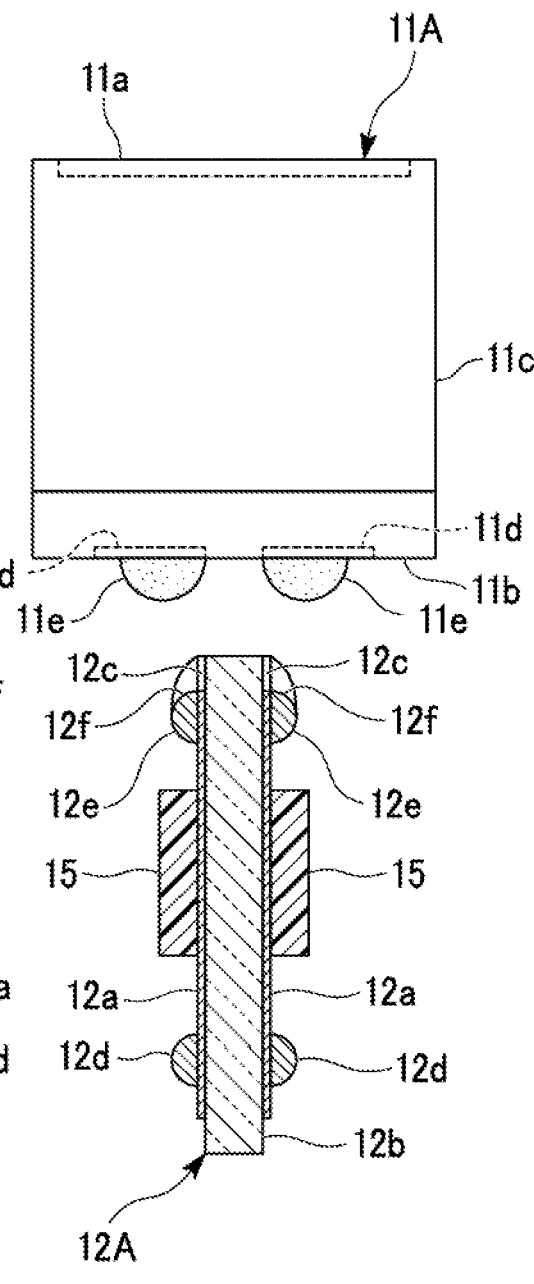

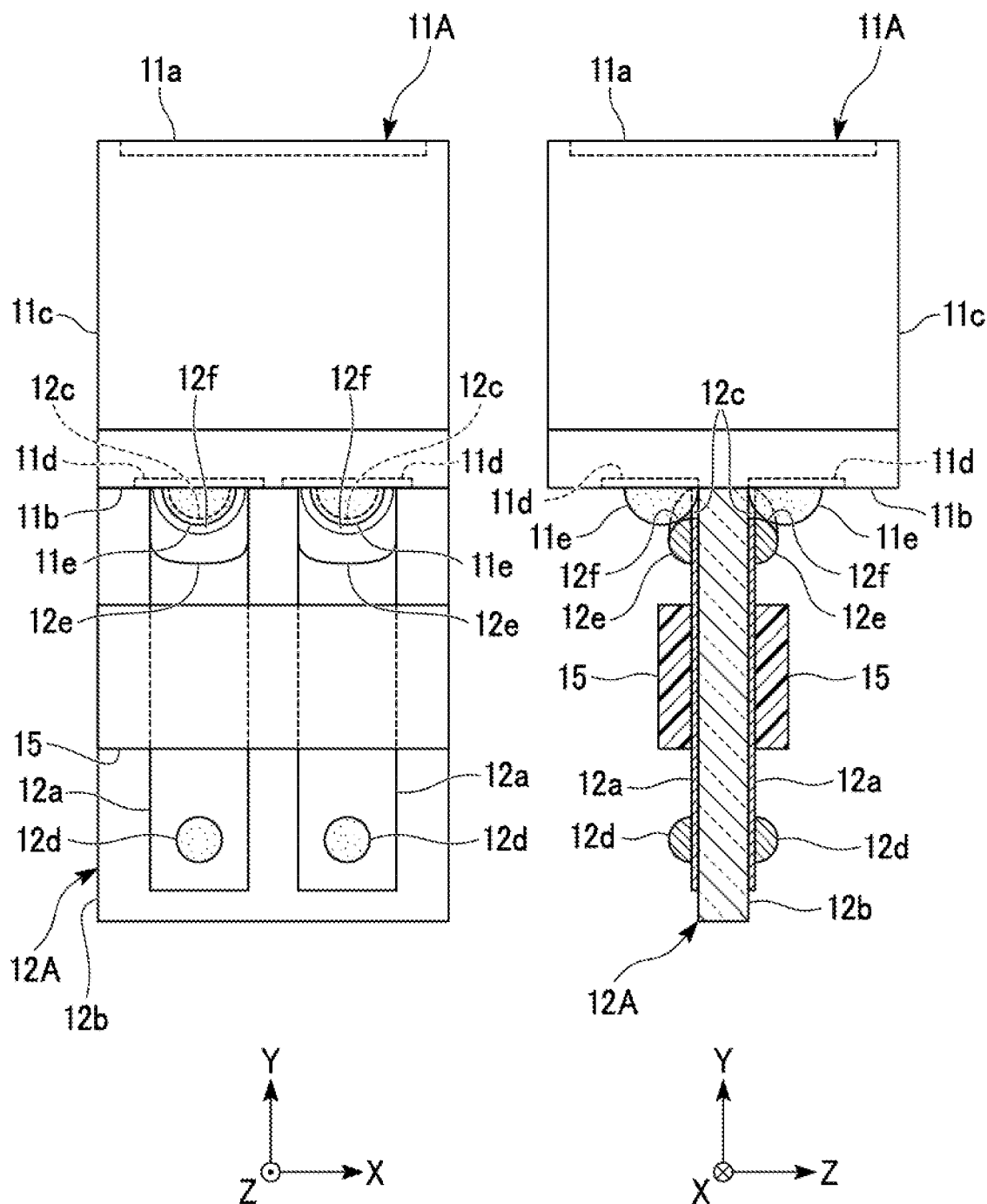

FIG. 6A
FIG. 6B
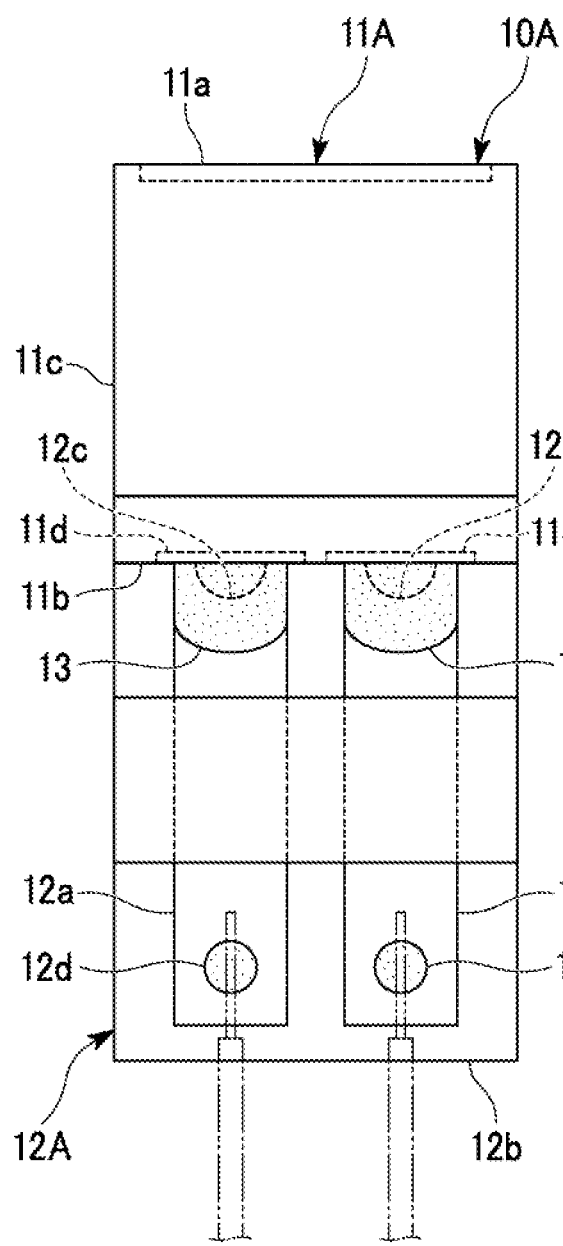
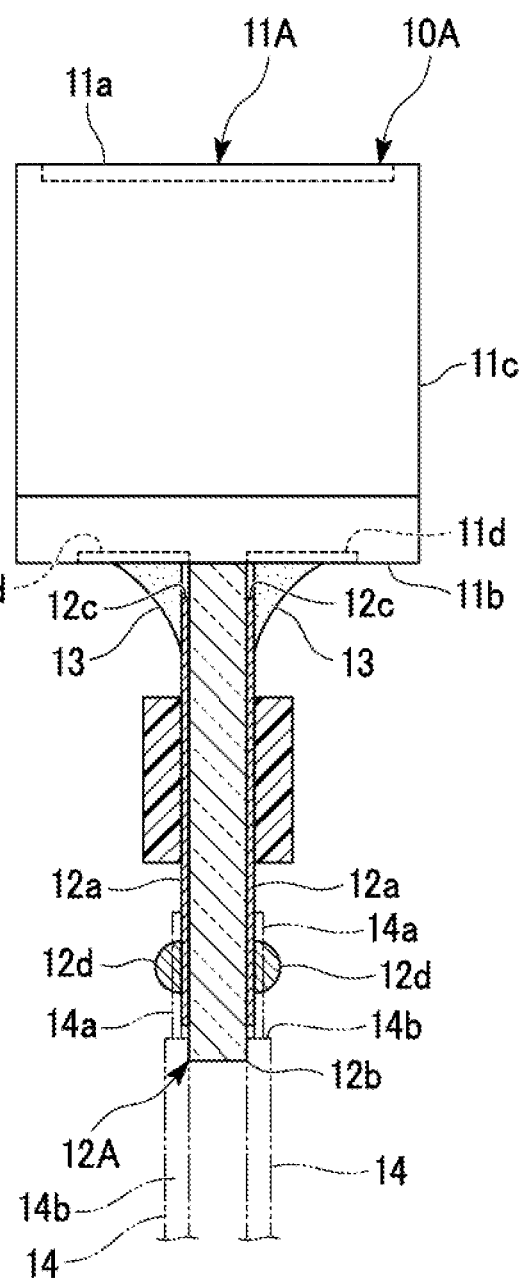
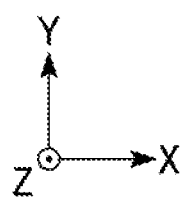
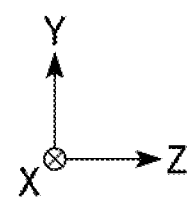

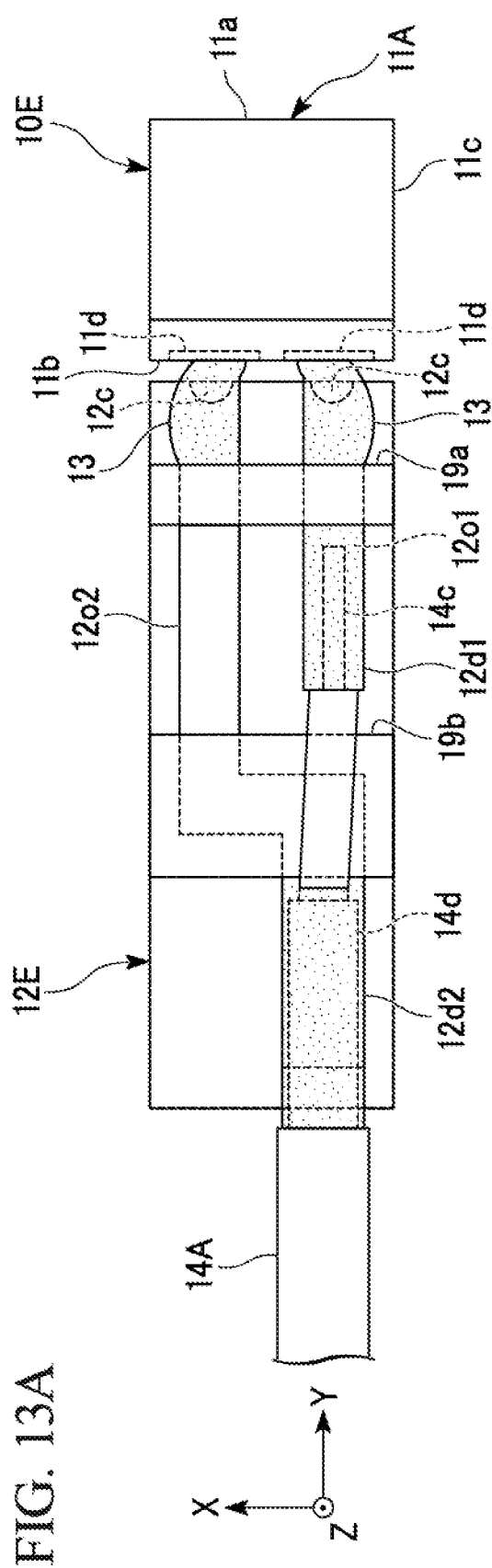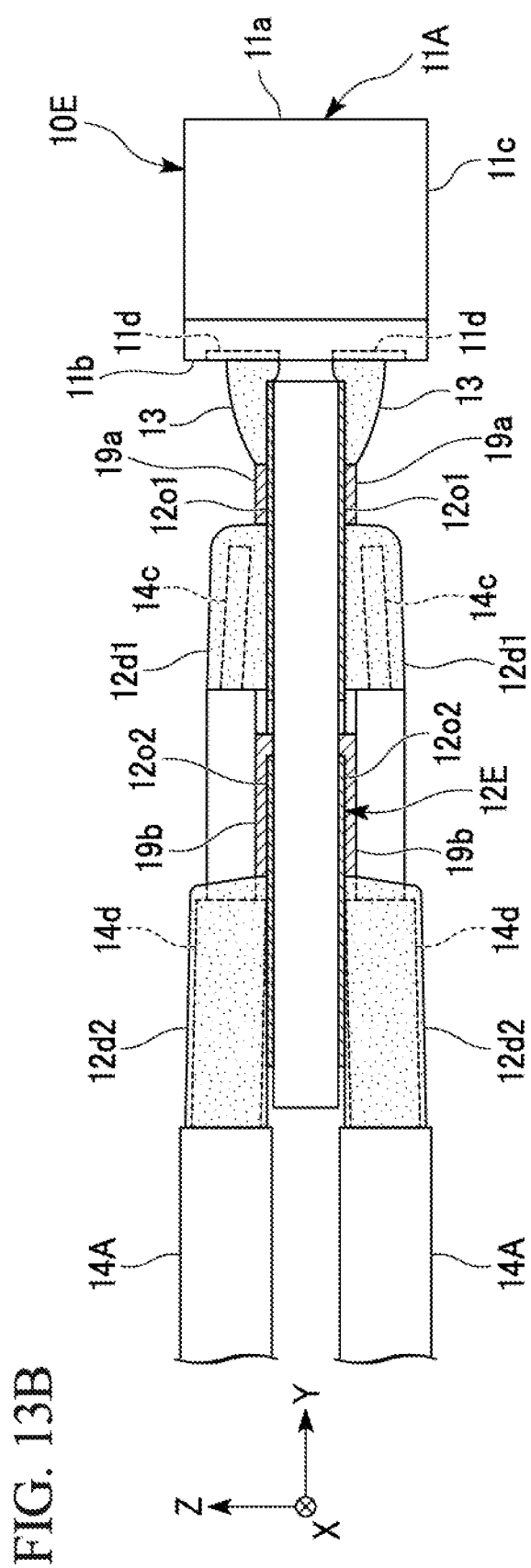

IMAGING MODULE AND METHOD OF MANUFACTURING THE SAME

CROSS REFERENCE TO RELATED APPLICATIONS

This application claims priority from Japanese Patent Application No. 2017-140297, filed Jul. 19, 2017, the content of which is incorporated herein by reference.

BACKGROUND OF THE INVENTION

Field of the Invention

The present invention relates to an imaging module that can be used for an endoscope or the like and has a configuration in which a solid-state imaging element is electrically connected to an electric cable via a wiring substrate, and to a method of manufacturing the imaging module.

Description of the Related Art

In an electronic endoscope, an imaging module having a configuration in which a solid-state imaging element (hereinafter also simply referred to as an imaging element) is electrically connected to a distal end of an electric cable via a wiring substrate is widely employed.

In this type of imaging module, a configuration in which a flexible wiring board is used for a wiring substrate (for example, Japanese Unexamined Patent Application, First Publication No. 2011-217887, hereinbelow, referred to as Patent Document 1) and a configuration in which a multilayer substrate is used for a wiring substrate (for example, Japanese Unexamined Patent Application, First Publication No. 2000-199863, hereinbelow, referred to as Patent Document 2, and Japanese Patent No. 5926890, hereinbelow, referred to as Patent Document 3) are known.

Patent Document 1 discloses an imaging module (imaging device) having a structure in which an imaging element having through wiring formed therein is used, portions on both sides (extended portions) are bent toward a side opposite to the imaging element via an intermediate portion on which the imaging element is mounted on a flexible substrate, and a signal cable connected to the extended portions of the flexible substrate and the imaging element are electrically connected via the wiring formed in the flexible substrate.

Patent Document 2 discloses an imaging module (solid-state imaging device) utilizing a T-shaped multilayer substrate having a horizontally oriented substrate on a rear surface of a vertically oriented substrate, and a film with a wiring pattern for electrically connecting between bonding pads provided on each of an imaging element outer peripheral portion and the rear surface of the vertically oriented substrate coupled to an imaging element rear surface.

In this imaging module (solid-state imaging device), a signal cable connected to a portion of the wiring provided on the multilayer substrate positioned on the horizontally oriented substrate and the imaging element are electrically connected via the wiring provided on the multilayer substrate and the wiring pattern of the film with the wiring pattern.

Patent Document 3 discloses an imaging module (imaging device) having a configuration in which a multilayer substrate having a core is used and an imaging element connected to an electrode member exposed on a side surface of the multilayer substrate and a wiring cable are electrically connected via the core of the multilayer substrate.

Patent Document 1 also discloses a configuration in which a block is fixedly adhered to an inside of the flexible substrate formed to be bent in a U shape.

According to this configuration, a shape of the flexible substrate can be stably maintained, and mounting accuracy of the imaging element with respect to the intermediate portion of the flexible substrate can be secured.

However, with this configuration, a block processed with high accuracy is required for securing the mounting accuracy of the imaging element, and it is necessary to accurately fix the flexible substrate to the block, and which is troublesome to assemble.

In the techniques disclosed in Patent Documents 2 and 3, the structure of the multilayer substrate is complicated and the multilayer substrate itself is not able to be manufactured easily.

In the imaging module (solid-state imaging device) disclosed in Patent Document 2, an extremely large number of layers are required to form the T-shaped multilayer substrate, which is not suitable for miniaturization and also causes a significant cost increase.

Further, although the number of layers decreases when a method of laminating substrates is used for manufacturing the T shape, since it is difficult to secure positional accuracy of the lamination and to stabilize the amount of exudation of adhesive for laminating, manufacturing it with sufficient accuracy is not easy.

The multilayer substrate disclosed in Patent Document 3 is extremely difficult to manufacture in that many processes are required for manufacturing and, from a viewpoint of miniaturization, since a plurality of electrode members are disposed in a narrow range, there is a high likelihood of the electrode members being stretched resulting in a short-circuit when the electrode members are cut.

SUMMARY OF THE INVENTION

An object of the invention is to provide an imaging module in which the imaging element terminal is able to be easily and reliably positioned with respect to the substrate terminal when the imaging element is mounted on the substrate, and a method of manufacturing the imaging module.

In order to solve the above problems, the invention provides the following aspects.

An imaging module according to a first aspect includes an imaging element, and a substrate positioned on a rear surface opposite to an imaging surface of the imaging element and provided to extend from the rear surface to a side opposite to the imaging surface, in which an electrode pad provided on the rear surface of the imaging element and a front end portion of an electrode pad provided on a main surface of the substrate at a position close to the imaging element are electrically connected via a conductive connecting material portion, and a notch portion recessed from a distal end of the front end portion is formed at the front end portion of the electrode pad of the substrate.

The imaging element may include the electrode pads on both sides of the rear surface with the front end portion of the substrate at a position close to the imaging element interposed therebetween, and the front end portions of the electrode pads each provided on main surfaces on both sides of the substrate may be electrically connected to the electrode pads of the imaging element via the conductive connecting material portions, respectively.

An electrically insulating inter-pad insulating wall portion may be provided between the electrode pads adjacent to each other at the front end portion of the main surface of the substrate.

The notch portions of the electrode pads adjacent to each other at the front end portion of the main surface of the substrate may be formed in a shape recessed from portions facing each other at regions including the distal ends of the adjacent electrode pads.

The substrate may include a cable connection terminal provided on the electrode pad to be spaced rearward from the notch portion, and an electronic component connection terminal provided at a position between the conductive connecting material portion of the electrode pad and the cable connection terminal.

An electric cable connected to a position spaced rearward from the notch portion of the electrode pad of the substrate may be further provided.

The electric cable may be a coaxial cable and may include an electrode pad having an internal conductor of the coaxial cable connected to a rear end portion thereof, and an electrode pad having an external conductor of the coaxial cable connected to the rear end portion thereof on the main surface of the substrate, and the rear end portion of the electrode pad to which the internal conductor of the coaxial cable is connected may be positioned on a front side of the rear end portion of the electrode pad to which the external conductor of the coaxial cable is connected.

A method of manufacturing an imaging module according to a second aspect includes a positioning step of bringing a solder terminal formed on an electrode pad provided on a main surface of a substrate into contact with a solder terminal formed on an electrode pad provided on a rear surface opposite to an imaging surface of an imaging element so that the substrate positioned on the rear surface of the imaging element and disposed in a direction extending from the rear surface to a side opposite to the imaging surface is positioned with respect to the imaging element, a step of forming a conductive connecting material portion electrically connecting the electrode pad of the imaging element to the electrode pad of the substrate, in which the solder terminal of the imaging element and the solder terminal of the substrate are heat-melted to be integrated and then cooled and solidified while maintaining the positioning state of the substrate with respect to the imaging element in the positioning step, and a notch portion formation step in which the solder terminal of the substrate is formed at a front end portion of the electrode pad of the substrate at a position close to the imaging element and a notch portion recessed from a front end at a position close to the imaging element is formed at the front end portion of the electrode pad and the solder terminal on the substrate, in which, in the positioning step, the substrate is positioned with respect to the imaging element by bringing the front end portion of the electrode pad and an edge portion of the solder terminal facing the notch portion which are on the substrate into contact with the solder terminal of the imaging element.

In the positioning step, the substrate may be positioned with respect to the imaging element by disposing the front end portion of the substrate at a position close to the imaging element between a plurality of solder terminals provided on the rear surface of the imaging element to be spaced apart from each other and by bringing the front end portion of the electrode pad provided on the main surfaces on both sides and an edge portion of the solder terminal facing the notch portion which are on the substrate into contact with the solder terminal of the imaging element.

Effects of the Invention

According to the imaging module and the method of manufacturing the imaging module according to the aspect of the invention, a front end portion of an electrode pad provided on the main surface of the substrate extending from the rear surface of the imaging element to a side opposite to the image surface of the imaging element is soldered to a solder terminal formed on the electrode pad provided on the rear surface of the imaging element. At this time, a notch portion positioned at the front end portion of the electrode pad provided on the substrate can be used for positioning the front end portion of the electrode pad provided on the substrate with respect to the solder terminal positioned on the rear surface of the imaging element.

When a solder terminal is provided at the front end portion of the electrode pad provided on the substrate that is to be soldered to a solder terminal on the rear surface of the imaging element, it is possible to employ a configuration in which a notch portion recessed from a front end of the front end portion is formed at the front end portion of the electrode pad provided on the substrate and the solder terminal provided on the front end portion of the electrode pad.

When this configuration is employed, by bringing the front end portion of the electrode pad and an edge portion of the solder terminal facing the notch portion which are provided on the substrate into contact with the solder terminal positioned on the rear surface of the imaging element, positioning of the front end portion (and the solder terminal) of the electrode pad provided on the substrate can be easily and accurately performed on the solder terminal positioned on the rear surface of the imaging element.

In addition, since the notch portion positioned at the front end portion of the electrode pad provided on the substrate main surface can accommodate at least a portion of the solder portion that electrically connects the electrode pad positioned on the rear surface of the imaging element to the front end portion of the electrode pad provided on the substrate main surface, the portion accommodated in the notch portion of the solder portion can be integrally joined to a notch portion inner circumferential surface.

As a result, for example, as compared with a case in which there is no notch portion at the front end portion of the electrode pad provided on the substrate main surface and the solder portion for electrically connecting the electrode pad positioned on the rear surface of the imaging element to the front end portion of the electrode pad provided on the substrate main surface is joined and integrated on only a surface of the front end portion of the electrode pad (a surface on a side opposite to the substrate) provided on the substrate main surface, a peeling strength (proof stress in a peeling direction) in a lifting direction with respect to the front end portion of the electrode pad provided on the substrate main surface of the imaging element can be enhanced, thereby effectively contributing to long-term stability maintenance and improvement of reliability in the electrical connection between the imaging element and the substrate.

BRIEF DESCRIPTION OF THE DRAWINGS

FIG. 1A is a plan view showing an imaging module according to a first embodiment of the invention.

FIG. 1B is a side view showing the imaging module according to the first embodiment of the invention.

FIG. 3A is a plan view showing an imaging element mounting step in the method of manufacturing the imaging module shown in FIGS. 1A and 1B.

FIG. 3B is a side view showing the imaging element mounting step in the method of manufacturing the imaging module shown in FIGS. 1A and 1B.

FIG. 4A is a plan view showing an imaging element and a substrate used in a method of manufacturing an imaging module according to a second embodiment of the invention.

FIG. 4B is a side view showing an imaging element and a substrate used in a method of manufacturing an imaging module according to the second embodiment of the invention.

FIG. 5A is a plan view showing a state in which a substrate electrode terminal is brought into contact with an element electrode terminal in a positioning step in a method of manufacturing the imaging module shown in FIGS. 4A and 4B.

FIG. 5B is a side view showing a state in which a substrate electrode terminal is brought into contact with an element electrode terminal in a positioning step in a method of manufacturing the imaging module shown in FIGS. 4A and 4B.

FIG. 6A is a plan view showing an imaging module according to the second embodiment of the invention obtained by executing an imaging element mounting step from a state shown in FIGS. 5A and 5B.

FIG. 6B is a side view showing an imaging module according to the second embodiment of the invention obtained by executing the imaging element mounting step from a state shown in FIGS. 5A and 5B.

FIG. 13A is a plan view showing a substrate having a configuration in which an internal conductor electrode pad having an internal conductor of a coaxial cable connected to a rear end portion thereof and an external conductor electrode pad having an external conductor of the coaxial cable connected to the rear end portion thereof are provided, and showing an imaging module assembled using the substrate.

FIG. 13B is a side view showing the substrate having a configuration in which the internal conductor electrode pad having an internal conductor of the coaxial cable connected to the rear end portion thereof and the external conductor electrode pad having an external conductor of the coaxial cable connected to the rear end portion thereof are provided, and showing an imaging module assembled using the substrate.

DETAILED DESCRIPTION OF THE INVENTION

Figure 2A:
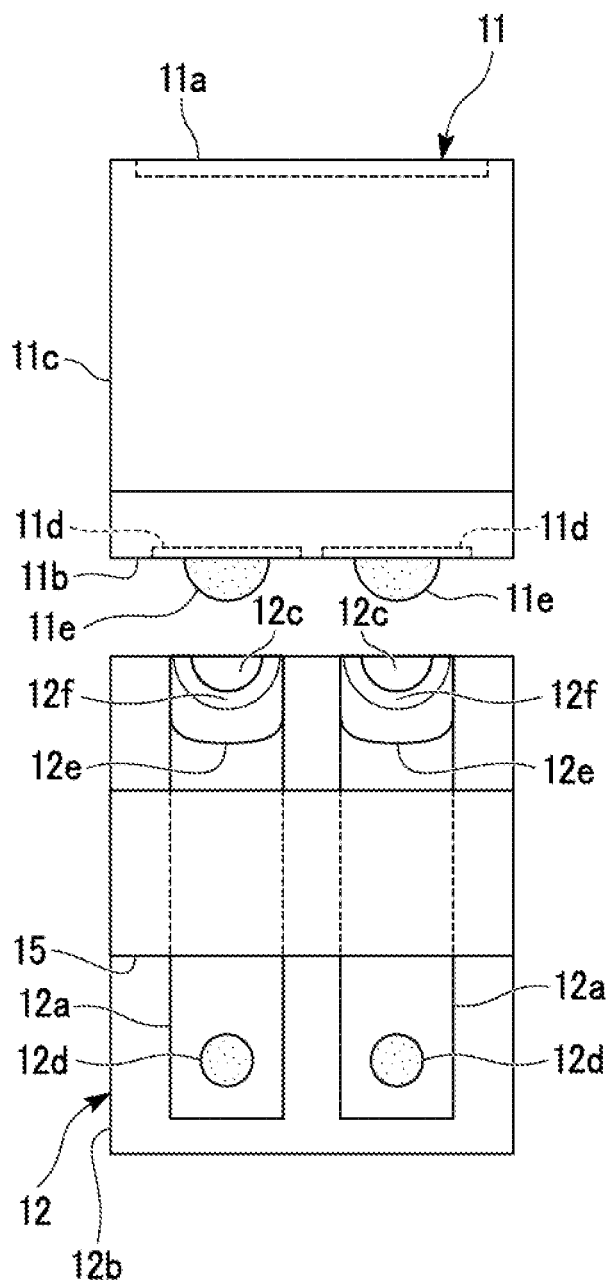
FIG. 2A is a plan view showing a state in which a substrate electrode terminal is brought into contact with an element electrode terminal in a positioning step in a method of manufacturing the imaging module shown in FIGS. 1A and 1B.

Hereinafter, an imaging module and a method of manufacturing the imaging module according to embodiments of the invention will be described with reference to the drawings.

In addition, an XYZ orthogonal coordinate system is set in FIGS. 1A to 13B.

In the present specification, hereinafter, description will be made assuming that an X direction is a width direction, a Y direction is a front-rear direction, and a Z direction is a height direction in the XYZ orthogonal coordinate system.

FIGS. 1A and 1B show an example of an imaging module 10 according to an embodiment of the invention.

FIGS. 2A to 3B are views for describing a method of manufacturing the imaging module 10 shown in FIGS. 1A and 1B.

As shown in FIGS. 1A and 1B, the imaging module 10 (imaging module according to a first embodiment) includes an imaging element 11, and a substrate 12 positioned on a rear surface 11b opposite to an imaging surface 11a of the imaging element 11 and provided to extend rearward (a side opposite to the imaging surface 11a) from the rear surface 11b.

The imaging element 11 includes an element main body 11c formed in a block shape.

The imaging surface 11a of the imaging element 11 is positioned on a front end surface of the element main body 11c.

The rear surface 11b of the imaging element 11 is a surface (rear surface) opposite to the front end surface of the element main body 11c.

Hereinafter, the rear surface 11b of the imaging element 11 is also referred to as a rear surface of the element main body 11c.

The imaging element 11 includes an electrode pad 11d (hereinafter also referred to as an element electrode pad) formed on the rear surface 11b of the element main body 11c.

On one side of a pair of main surfaces of the substrate 12, electrode pads 12a (hereinafter also referred to as substrate electrode pads) extending in the front-rear direction (Y direction) are formed at a plurality of positions (two positions in FIGS. 1A and 1B) spaced apart from each other in the width direction (X direction) of the substrate 12.

The substrate 12 includes an electrically insulating plate 12b and the electrode pads 12a formed on one side of the main surfaces on both sides of the insulating plate 12b.

The main surfaces of the substrate 12 are main surfaces of the insulating plate 12b.

On the other hand, a plurality of element electrode pads 11d on the rear surface 11b of the imaging element 11 are provided to correspond to a plurality of substrate electrode pads 12a at a front end portion (end portion positioned close to the imaging element) of the substrate 12.

The imaging module 10 shown in FIGS. 1A and 1B has a configuration in which the imaging element 11 is mounted on the substrate 12 by the front end portions (end portions positioned close to the imaging element) of the substrate electrode pads 12a and the element electrode pads 11d being respectively joined and electrically connected by a thermally fusible conductive connecting material portion 13.

The conductive connecting material portion 13 is provided between each of the front end portions of the substrate electrode pads 12a and each of the element electrode pads 11d so that the front end portion of the substrate electrode pad 12a and the element electrode pad 11d are electrically connected and fixedly joined to each other.

Further, the substrate 12 is supported by the conductive connecting material portion 13 in a direction extending rearward from the rear surface 11b of the imaging element 11 with respect to the imaging element 11.

The conductive connecting material portion 13 is, for example, a thermally fusible conductive metal material (including an alloy) having a melting point lower than 450° C. such as solder or the like.

The conductive connecting material portion 13 joins and electrically connects conducting metals to each other by cooling and solidifying from a molten state due to, for example, inclusion of flux or the like.

As shown in FIGS. 1A and 1B, a notch portion 12c recessed from a distal end (front end) of the front end portion is formed at the front end portion of the substrate electrode pad 12a.

The notch portion 12c shown in FIGS. 1A and 1B is formed in a semicircular shape recessed from the front end of the substrate electrode pad 12a.

The notch portion 12c shown in FIGS. 1A and 1B is formed between both end portions in the width direction of the front end portion of the substrate electrode pad 12a.

The entire substrate electrode pad 12a is positioned on the main surface of the insulating plate 12b.

The front ends of the portions on both sides in the width direction of the substrate electrode pad 12a are positioned at the front end of the insulating plate 12b via both end portions in the width direction of the front end portion of the substrate electrode pad 12a, that is, the notch portion 12c positioned at the front end portion of the substrate electrode pad 12a.

One side of the substrate electrode pad 12a in the thickness direction (coincides with a height direction) of the notch portion 12c positioned at the front end portion of the substrate electrode pad 12a is blocked by the insulating plate 12b.

In FIGS. 1A and 1B, the notch portion 12c is covered with the conductive connecting material portion 13.

Further, a formation material of the conductive connecting material portion 13 is buried in the notch portion 12c.

A portion of the conductive connecting material portion 13 positioned in the notch portion 12c is fixed to an inner circumferential surface of the notch portion 12c.

As shown by a virtual line (double dotted-dashed line) in FIGS. 1A and 1B, a conductor 14a of an electric cable 14 can be connected (electrically connected) to a rear end portion of the substrate electrode pad 12a.

A thermally fusible cable connection terminal 12d for connecting the conductor 14a of the electric cable 14 is provided at the rear end portion of the substrate electrode pad 12a.

As a formation material of the cable connection terminal 12d, for example, a material that can be employed as the formation material of the conductive connecting material portion 13, such as solder, can be used.

The cable connection terminal 12d is formed by overlaying the formation material of the cable connection terminal 12d on a surface side opposite to the insulating plate 12b at the rear end portion of the substrate electrode pad 12a.

As shown in FIGS. 1A and 1B, the electric cable 14 includes a sheath 14b covering a surrounding periphery of the conductor 14a.

The conductor 14a exposed at a distal end of the sheath 14b of the electric cable 14 is fixedly joined to the rear end portion of the substrate electrode pad 12a by the formation material of the cable connection terminal 12d (fixed by cooling and solidification after heat-melting (reflow) of the cable connection terminal 12d) and is electrically connected thereto.

In FIGS. 1A and 1B, the cable connection terminal 12d formed in a hemispherical shape at the rear end portion of the substrate electrode pad 12a is an exemplary example.

However, a shape of the cable connection terminal is not limited to a hemispherical shape, and, for example, a shape formed in a layered form having a substantially constant layer thickness at the rear end portion of the substrate electrode pad 12a may be employed.

The electrical connection of the conductor 14a of the electric cable 14 to the rear end portion of the substrate electrode pad 12a is not limited to a connection structure using the thermally fusible cable connection terminal 12d, and may be performed using a conductive adhesive, for example.

In a case of using a conductive adhesive, for example, in place of the cable connection terminal 12d, a cable connection terminal on which a conductive adhesive is overlaid is provided at the rear end portion of the substrate electrode pad 12a.

Then, by heating and curing the cable connection terminal while maintaining a state of the conductor 14a of the electric cable 14 being in contact with the cable connection terminal, the conductor 14a of the electric cable 14 is fixedly joined to the rear end portion of the substrate electrode pad 12a via the cable connection terminal.

The imaging module may include the electric cable 14 electrically connected by fixedly joining the conductor 14a to the rear end portion of the substrate electrode pad 12a.

The conductor 14a of the electric cable 14 connected to the rear end portion of the substrate electrode pad 12a is electrically connected to an electric circuit of the element main body 11c of the imaging element 11 via the substrate electrode pad 12a and the element electrode pad 11d.

Figure 2B:
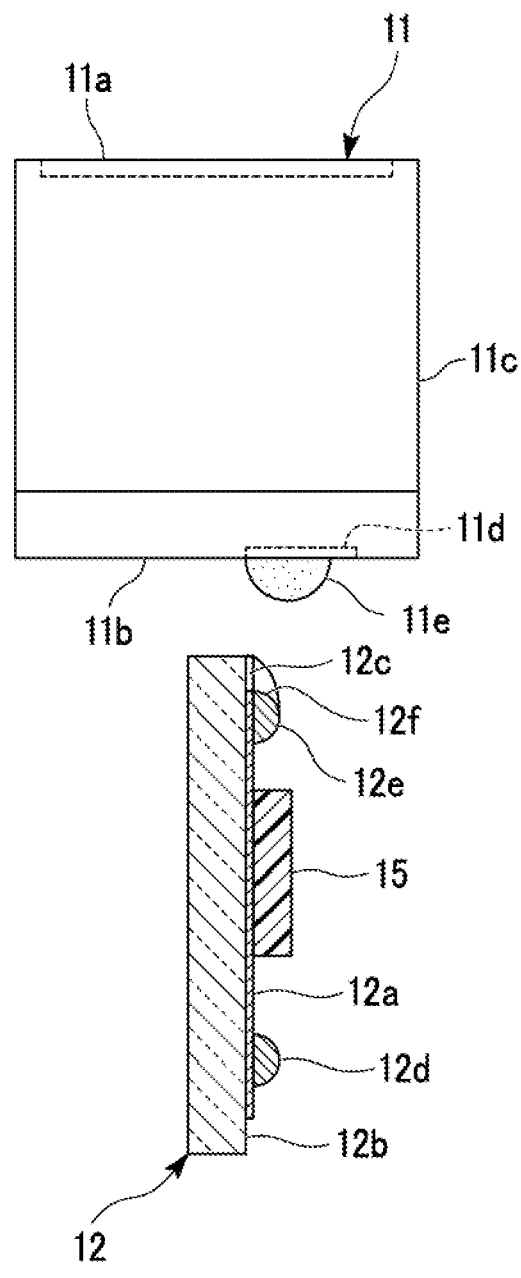
FIG. 2B is a side view showing a state in which the substrate electrode terminal is brought into contact with the element electrode terminal in the positioning step in a method of manufacturing the imaging module shown in FIGS. 1A and 1B.

FIGS. 2A and 2B show the imaging element 11 and the substrate 12 in a state before being connected to each other.

In FIGS. 2A and 2B, the imaging element 11 includes a thermally fusible electrode terminal 11e (also referred to as an element electrode terminal) formed to protrude from the element electrode pad 11d.

Configurations other than the element electrode terminal 11e shown in FIGS. 2A and 2B are the same as those of the imaging element 11 in the state shown in FIGS. 1A and 1B (the state in which the imaging element 11 is mounted on the substrate 12).

The element electrode terminal 11e is formed using a formation material that can be employed for the conductive connecting material portion 13.

The element electrode terminal 11e is formed in a hemispherical shape by overlaying the formation material of the element electrode terminal 11e on a rear surface side of the element electrode pad 11d (a side opposite to the imaging surface 11a, a rear side).

For the element electrode terminal 11e, for example, a solder bump or the like can be employed.

A thermally fusible electrode terminal 12e (hereinafter also referred to as a substrate electrode terminal) is provided at the front end portion of the substrate electrode pad 12a of the substrate 12 shown in FIGS. 2A and 2B.

Configurations other than the substrate electrode terminal 12e of the substrate 12 shown in FIGS. 2A and 2B are the same as those of the substrate 12 in the state shown in FIGS. 1A and 1B (the state in which the imaging element 11 is mounted on the substrate 12).

The substrate electrode terminal 12e is formed using a formation material that can be employed for the conductive connecting material portion 13.

The substrate electrode terminal 12e is formed by overlaying a formation material of the substrate electrode terminal 12e on a surface side opposite to the insulating plate 12b at the front end portion of the substrate electrode pad 12a.

For the substrate electrode terminal 12e, for example, a solder bump or the like can be employed.

Further, the substrate electrode pad 12a is formed on the main surface of the insulating plate 12b to extend rearward from the front end of the main surface of the insulating plate 12b.

The front end portion of the substrate electrode pad 12a is positioned at the front end portion (the front end portion of the substrate 12) of the insulating plate 12b.

A portion of the substrate electrode terminal 12e is formed conforming to an edge portion facing the notch portion 12c (hereinafter also referred to as a substrate pad notch portion) positioned at the front end portion of the substrate electrode pad 12a.

A notch portion 12f recessed from the front end is formed in the substrate electrode terminal 12e along an inner circumference (an edge portion of the substrate electrode pad 12a facing the notch portion 12c) of the substrate pad notch portion 12c.

Hereinafter, the notch portion 12f of the substrate electrode terminal 12e is also referred to as an electrode terminal notch portion or a substrate electrode terminal notch portion.

Next, a method of forming the substrate electrode terminal 12e on the front end portion of the substrate electrode pad 12a will be described.

First, the formation material of the substrate electrode terminal 12e in a heat-melted state is placed on a surface side of the front end portion of the substrate electrode pad 12a on which the notch portion 12c is formed. Alternatively, the formation material of the substrate electrode terminal 12e provided in a solidified state on the surface side of the front end portion of the substrate electrode pad 12a is heat-melted, and this is referred to as a state in which the formation material of the substrate electrode terminal 12e in a heat-melted state is provided on the surface side of the front end portion of the substrate electrode pad 12a.

Here, the formation material of the substrate electrode terminal 12e in the heat-melted state has a shape in which a notch portion recessed along the inner circumference of the substrate pad notch portion 12c is formed due to a surface tension of the formation material.

Next, the formation material of the substrate electrode terminal 12e in a shape in which the notch portion is formed is cooled and solidified to obtain the substrate electrode terminal 12e having the notch portion 12f.

Further, as the formation material of the substrate electrode terminal 12e, a material which has good wettability with respect to the substrate electrode pad 12a in a heat-melted state and is firmly fixed to the surface of the substrate electrode pad 12a when cooled and solidified is employed.

As a material of the insulating plate 12b, a material which has the low wettability of the formation material of the substrate electrode terminal 12e in a heat-melted state with respect to the main surface of the insulating plate 12b and on which the formation material of the substrate electrode terminal 12e cooled and solidified from the heat-melted state does not fix is employed.

As a result, with the formation material of the substrate electrode terminal 12e in a heat-melted state provided at the front end portion of the substrate electrode pad 12a, a recessed portion along the inner circumference of the substrate pad notch portion 12c can be easily formed and the substrate electrode terminal 12e having the electrode terminal notch portion 12f can be easily obtained.

The notch portion 12f of the substrate electrode terminal 12e shown in FIGS. 2A and 2B is a concave portion recessed in a semicircular shape from the front end of the substrate electrode terminal 12e along the inner circumference of the semicircular substrate pad notch portion 12c (edge portion of the substrate electrode pad 12a facing the notch portion 12c).

The substrate electrode terminal 12e is formed to be present over the entire length of the end edge facing the notch portion 12c of the substrate electrode pad 12a.

The substrate electrode terminal 12e shown in FIGS. 2A and 2B is formed on the entire front end portion of the substrate electrode pad 12a.

The substrate electrode terminal 12e is formed in a substantially hemispherical shape (partially notched hemispherical shape) having the electrode terminal notch portion 12f.

The inner circumference of the notch portion 12f of the substrate electrode terminal is formed to be curved in a concave shape conforming to the edge portion facing the substrate pad notch portion 12c of the substrate electrode pad 12a.

An inner circumferential portion of the substrate electrode terminal 12e is formed to extend over the entire edge portion facing the semicircular notch portion 12c at the front end portion of the substrate electrode pad 12a.

Specifically, the notch portion 12f of the substrate electrode terminal 12e shown in FIGS. 2A and 2B is formed in a tapered shape in which an inner diameter increases in a direction from the substrate pad notch portion 12c toward a side opposite to the insulating plate 12b of the substrate 12.

However, it is also possible to employ a configuration in which the inner diameter of the electrode terminal notch portion 12f is constant in a thickness direction (height direction) of the substrate 12.

The imaging module 10 shown in FIGS. 1A and 1B has a structure in which the element electrode pad 11d of the imaging element 11 is connected (electrically connected) and fixedly joined to the front end portion of the substrate electrode pad 12a of the substrate 12 shown in FIGS. 2A and 2B by the conductive connecting material portion 13, and thereby the imaging element 11 is mounted on the substrate 12.

In a method of connecting the element electrode pad 11d to the front end portion of the substrate electrode pad 12a, in a state in which the electrode terminals 11e and 12e respectively provided on the front end portion of the substrate electrode pad 12a and the element electrode pad 11d are brought into contact with each other, the conductive connecting material portion 13 is formed by cooling and solidifying the member that has been integrated by heat-melting (reflow). Thereby, connection of the element electrode pad 11d to the front end portion of the substrate electrode pad 12a is realized.

Next, a method of manufacturing the imaging module 10 (method of manufacturing the imaging module according to the first embodiment) using the substrate 12 and the imaging element 11 shown in FIGS. 2A and 2B will be described. First, as shown in FIGS. 3A and 3B, a positioning step of positioning the imaging element 11 with respect to the substrate 12 is performed by inserting the electrode terminal 11e of the imaging element 11 into the notch portion 12f of the substrate electrode terminal 12e and bringing it into contact with the substrate electrode terminal 12e.

In the positioning step, for example, with respect to the imaging element 11 supported at a predetermined position by a support tool, the substrate 12 disposed on the rear surface side of the imaging element 11 is disposed to be oriented vertically with respect to the imaging element rear surface 11b and is moved forward to the imaging element rear surface 11b while maintaining the arrangement state of the substrate. Thereby, the substrate electrode terminal 12e is brought into contact with the element electrode terminal 11e inserted into the notch portion 12f of the substrate electrode terminal.

As shown in FIGS. 3A and 3B, in the positioning step, a portion of the hemispherical element electrode terminal 11e inserted into the notch portion 12f of the substrate electrode terminal is brought into contact with an inner circumferential surface of the notch portion 12f of the substrate electrode terminal 12e.

The element electrode terminal 11e is brought into contact with a rearmost portion in the front-rear direction of a cross section perpendicular to the height direction (Z direction) of the inner circumferential surface of the notch portion 12f of the substrate electrode terminal.

In the cross section perpendicular to the height direction (Z direction) of the notch portion 12f, the notch portion 12f of the substrate electrode terminal is formed in a semicircular shape having an inner circumferential surface securing a radius of curvature which allows the hemispherical element electrode terminal 11e to be inserted and brought into contact with the rearmost portion in the front-rear direction.

In the positioning step shown in FIGS. 3A and 3B, specifically, the element electrode terminal 11e is inserted into the substrate pad notch portion 12c and the notch portion 12f of the substrate electrode terminal, a portion of the element electrode terminal 11e inserted into the notch portion 12f of the substrate electrode terminal is brought into contact with the inner circumferential surface of the notch portion 12f of the substrate electrode terminal, and the portion inserted into the substrate pad notch portion 12c is brought into contact with a portion of the insulating plate 12b exposed to the substrate pad notch portion 12c.

When the element electrode terminal 11e is brought into contact with the inner circumferential surface of the notch portion 12f of the substrate electrode terminal and a portion of the insulating plate 12b exposed to the substrate pad notch portion 12c, the front end of the substrate 12 is disposed close to the rear surface 11b of the imaging element 11 (hereinafter also referred to as an imaging element rear surface) via a slight clearance (not shown) between the front end of the substrate 12 and the imaging element rear surface 11b, or is brought into contact with the imaging element rear surface 11b.

In the substrate pad notch portion 12c, a portion of the element electrode terminal 11e in a circumferential direction of a portion closer to the element electrode pad 11d than the portion of the element electrode terminal 11e inserted into the notch portion 12f of the substrate electrode terminal is inserted into the front end portion of the substrate pad notch portion 12c.

Further, in order to be capable of bringing the portion inserted into the substrate pad notch portion 12c in the element electrode terminal 11e brought into contact with the inner circumferential surface of the notch portion 12f of the substrate electrode terminal into contact with a portion of the insulating plate 12b exposed to the substrate pad notch portion 12c, the substrate pad notch portion 12c is formed to have a sufficient dimension in the width direction (X direction) secured at the front end portion of the substrate pad notch portion 12c.

A dimension in the width direction of the front end portion of the semicircular substrate pad notch portion 12c shown in FIGS. 2A and 2B is secured to be approximately equal to an outer diameter of the portion of the element electrode terminal 11e inserted into the substrate pad notch portion 12c (a portion to be inserted into the substrate pad notch portion 12c when it is brought into contact with the inner circumferential surface of the notch portion 12f of the substrate electrode terminal and a portion of the insulating plate 12b exposed to the substrate pad notch portion 12c).

The dimension in the width direction of the front end portion of the substrate pad notch portion 12c may be any size as long as the portion of the element electrode terminal 11e to be inserted into the substrate pad notch portion 12c can be brought into contact with a portion of the insulating plate 12b exposed to the substrate pad notch portion 12c, and may be equal to, slightly smaller than, or slightly larger than an outer diameter of the portion at which the element electrode terminal 11e is inserted into the substrate pad notch portion 12c.

As shown in FIGS. 3A and 3B, in the positioning step, the hemispherical element electrode terminal 11e is brought into contact with the inner circumferential surface of the notch portion 12f of the substrate electrode terminal and a portion of the insulating plate 12b exposed to the substrate pad notch portion 12c, and the substrate 12 disposed on the rear surface side of the imaging element 11 is held in a direction extending rearward (a side opposite to the imaging surface 11a) from the imaging element 11 using a support tool or the like.

As shown in FIGS. 3A and 3B, in the positioning step, insertion of the element electrode terminal 11e into the notch portion 12f of the substrate electrode terminal 12e (also inserted into the substrate pad notch portion 12c in FIGS. 3A and 3 B) facilitates positioning of the substrate 12 in the width direction with respect to the imaging element 11.

For example, when the inner circumferential surface of the notch portion 12f of the substrate electrode terminal is in line contact with the element electrode terminal 11e inserted into the notch portion 12f of the substrate electrode terminal, positioning of the substrate 12 in the width direction with respect to the imaging element 11 can be completed by inserting the element electrode terminal 11e into the notch portion 12f of the substrate electrode terminal.

In addition, when an extremely narrow range of the inner circumferential surface of the notch portion 12f of the substrate electrode terminal is substantially in point contact with the element electrode terminal 11e inserted into the notch portion 12f of the substrate electrode terminal, rough positioning of the substrate 12 in the width direction with respect to the imaging element 11 can be performed.

Bringing the element electrode terminal 11e inserted into the notch portion 12f of the substrate electrode terminal 12e into contact with the substrate electrode terminal 12e (specifically, the inner circumferential surface of the notch portion 12f of the substrate electrode terminal 12e) realizes positioning of the substrate 12 in the front-rear direction with respect to the imaging element 11.

Bringing the portion of the element electrode terminal 11e inserted into the substrate pad notch portion 12c into contact with a portion of the insulating plate 12b of the substrate 12 exposed to the substrate pad notch portion 12c realizes positioning of the substrate 12 in the height direction (Z direction) with respect to the imaging element 11.

Therefore, in the positioning step, the element electrode terminal 11e is inserted into the substrate pad notch portion 12c and the notch portion 12f of the substrate electrode terminal, the element electrode terminal 11e is brought into contact with the inner circumferential surface of the notch portion 12f of the substrate electrode terminal and a portion of the insulating plate 12b exposed to the substrate pad notch portion 12c, and thereby positioning of the substrate 12 in the width direction, the front-rear direction, and the height direction with respect to the imaging element 11 can be easily and reliably performed.

The substrate 12 is a rigid substrate that cannot be easily bent due to an external force and maintains a plate-like state stably.

The substrate 12 maintains a plate-like state stably in the positioning step.

Therefore, with the positioning step, the element electrode terminal 11e is inserted into the notch portion 12f of the substrate electrode terminal 12e, the element electrode terminal 11e is brought into contact with the inner circumferential surface of the notch portion 12f of the substrate electrode terminal and a portion of the insulating plate 12b exposed to the substrate pad notch portion 12c, and thereby positioning of the substrate 12 with respect to the imaging element 11 can be easily and reliably performed.

In the positioning step using the substrate 12 shown in FIGS. 2A and 2B, the element electrode terminal 11e is inserted into the notch portion 12c and the electrode terminal notch portion 12f on each of the plurality of electrode pads 12a provided on one surface of the substrate 12 (a main surface on one side) and the element electrode terminal 11e is brought into contact with the substrate electrode terminal 12e and a portion of the insulating plate 12b exposed to the substrate pad notch portion 12c.

Insertion of the element electrode terminal 11e into the notch portion 12c and the electrode terminal notch portion 12f of each of the plurality of electrode pads 12a provided on the substrate 12 and bringing the element electrode terminal 11e into contact with the substrate electrode terminal 12e and the insulating plate 12b exposed to the substrate pad notch portion 12c effectively contribute to securing positioning accuracy of the substrate 12 with respect to the imaging element 11 and maintaining the stability of the substrate 12 in a direction with respect to the imaging element 11.

When the positioning step is completed, while maintaining the position and orientation of the substrate 12 with respect to the imaging element 11 using a support tool or the like, the element electrode terminal 11e and the substrate electrode terminal 12e are heat-melted (reflowed) to be integrated, and then cooled and solidified to perform an imaging element mounting step in which the conductive connecting material portion 13 (see FIGS. 1A and 1B) is formed.

When the imaging element mounting step is completed, electrical connection between the element electrode pad 11d and the substrate electrode pad 12a is reliably secured by the conductive connecting material portion 13, and the substrate 12 is supported in a direction in which the substrate 12 extends toward the rear side of the imaging element rear surface 11b with respect to the imaging element 11 by the conductive connecting material portion 13.

As a result, the imaging module 10 is assembled, and manufacture of the imaging module 10 is completed.

Fixedly joining and electrically connecting the conductor 14a of the electric cable 14 to the rear end portion of the substrate electrode pad 12a are performed, for example, after completion of the imaging element mounting step, but may also be performed by heat-melting (reflowing) the cable connection terminal 12d in parallel with the imaging element mounting step.

Fixedly joining and electrically connecting the conductor 14a of the electric cable 14 to the rear end portion of the substrate electrode pad 12a may also be performed before the positioning step or between the positioning step and the imaging element mounting step.

In the front-rear direction of the substrate 12 shown in FIGS. 2A and 2B, an electrically insulating front-rear insulating wall portion 15 is provided between the electrode terminal 12e and the cable connection terminal 12d.

The front-rear insulating wall portion 15 is formed of an electrically insulating material such as a resin.

The front-rear insulating wall portion 15 is formed by, for example, a resin layer provided on the main surface of the insulating plate 12b, or a protruding portion in which a portion of the insulating plate 12b protrudes to the main surface of the insulating plate 12b.

The front-rear insulating wall portion 15 is formed on the main surface of the substrate 12 to extend in the width direction of the main surface of the substrate 12.

The front-rear insulating wall portion 15 covers a central portion between the substrate electrode terminal 12e and the cable connection terminal 12d in the extending direction (front-rear direction) of the substrate electrode pad 12a.

The front-rear insulating wall portion 15 prevents a formation material (formation material of the conductive connecting material portion 13) of the substrate electrode terminal 12e and the element electrode terminal 11e which are heat-melted in a state of being in contact with each other from reaching the cable connection terminal 12d due to a flow of the formation material.

The front-rear insulating wall portion 15 can prevent the formation material of the conductive connecting material portion 13 in a heat-melted state from reaching the cable connection terminal 12d and affecting an electrical connection between the conductor 14a of the electric cable 14 and the rear end portion of the substrate electrode pad 12a due to the cable connection terminal 12d.

Further, a configuration in which the substrate 12 does not have the front-rear insulating wall portion 15 can also be employed.

As shown in FIGS. 1A and 1B, in the imaging element mounting step, a portion of the conductive connecting material portion 13 that has entered the substrate electrode pad notch portion 12c is fixed to the inner circumferential surface of the substrate electrode pad notch portion 12c.

The conductive connecting material portion 13 covers a surface of the front end portion of the substrate electrode pad 12a and the element electrode pad 11d, and includes a portion connecting the front end portion of the substrate electrode pad 12a and the element electrode pad 11d and a portion connecting the inner circumferential surface of the substrate electrode pad notch portion 12c and the element electrode pad 11d.

Therefore, in the imaging module 10, even when a displacement force acts between the imaging element 11 and the substrate 12 due to flowing or the like during processing, disconnection of the conductive connecting material portion 13 connecting between the front end portion of the substrate electrode pad 12a and the element electrode pad 11d does not easily occur.

As described above, the substrate 12 having the substrate electrode pad 12a in which the notch portion 12c is formed at the front end portion is employed. In addition, in the configuration of the conductive connecting material portion 13 connecting the substrate electrode pad 12a to the element electrode pad 11d, the surface of the front end portion of the substrate electrode pad 12a and the element electrode pad 11d are covered to secure a portion connecting the front end portion of the substrate electrode pad 12a and the element electrode pad 11d and a portion connecting the inner circumferential surface of the substrate electrode pad notch portion 12c and the element electrode pad 11d. This configuration is advantageous for maintaining a stable electrical connection between the substrate electrode pad 12a and the element electrode pad 11d and enhancing long-term reliability.

As shown in FIGS. 4A to 6B, an imaging module may utilize a substrate 12A having electrode pads 12a in which notch portions 12c are formed at front end portions on both sides of main surfaces, and may be assembled by fixedly joining and electrically connecting the front end portions of the electrode pads 12a of the substrate 12A respectively to electrode pads 11d of a rear surface 11b of the imaging element using conductive connecting material portions 13.

An imaging element 11A of an imaging module 10A (imaging module according to a second embodiment) shown in FIGS. 6A and 6B includes the electrode pads 11d provided on the rear surface 11b of the imaging element 11A to correspond to the respective electrode pads 12a on both sides of the substrate 12A.

In the imaging module 10A shown in FIGS. 6A and 6B, the front end portions of the electrode pads 12a of the substrate 12A are fixedly joined respectively to the electrode pads 11d of the imaging element 11A via the conductive connecting material portions 13 and are electrically connected.

FIGS. 4A and 4B show the imaging element 11A and the substrate 12A used for manufacturing the imaging module 10A shown in FIGS. 6A and 6B.

The substrate 12A shown in FIGS. 4A and 4B has a structure in which the electrode pads 12a, each having a notch portion 12c formed in the front end portion, and the substrate electrode terminals 12e are provided on the main surface on both sides of the substrate 12 shown in FIGS. 2A and 2B.

Configurations of the electrode pad 12a and the substrate electrode terminal 12e including shapes, arrangement, and the like on each main surface (main surfaces on both sides of an insulating plate 12b) of the substrate 12A are the same as those of the substrate 12 shown in FIG. 2A.

In addition, a configuration of including a cable connection terminal 12d and a front-rear insulating wall portion 15 is the same as that of the substrate 12 shown in FIG. 2A.

The imaging element 11A differs from the imaging element 11 shown in FIGS. 2A and 2B only in that a plurality of electrode pads 11d and electrode terminals 11e are provided on the rear surface 11b to correspond to the electrode pads 12a provided on the main surfaces on both sides of the substrate 12.

Next, a method of manufacturing the imaging module 10A shown in FIGS. 6A and 6B (a method of manufacturing an imaging module according to a second embodiment) using the imaging element 11A and the substrate 12A shown in FIGS. 4A and 4B will be described. First, as shown in FIGS. 5A and 5B, a positioning step of positioning the substrate 12A with respect to the imaging element 11A is performed.

Next, an imaging element mounting step in which the element electrode terminal 11e and the substrate electrode terminal 12e brought into contact with each other in the positioning step are heat-melted (reflowed) and then cooled and solidified to form the conductive connecting material portion 13 (see FIGS. 6A and 6 B) is performed.

As shown in FIGS. 5A and 5B, on the rear surface 11b of the imaging element 11A, the element electrode terminal 11e in contact with the substrate electrode terminal 12e provided on one main surface of the substrate 12A and the element electrode terminal 11e in contact with the substrate electrode terminal 12e provided on the other main surface of the substrate 12A are provided spaced apart from each other in a height direction (Z direction).

The separation distance between the element electrode terminal 11e in contact with the substrate electrode terminal 12e provided on one main surface of the substrate 12A and the element electrode terminal 11e in contact with the substrate electrode terminal 12e provided on the other main surface of the substrate 12A is set to be equal to or slightly larger than a plate thickness of the insulating plate 12b of the substrate 12A.

In the positioning step, the substrate 12A is inserted from a rear side of the element electrode terminals 11e between the element electrode terminal 11e in contact with the substrate electrode terminal 12e provided on one main surface of the substrate 12A and the element electrode terminal 11e in contact with the substrate electrode terminal 12e provided on the other main surface of the substrate 12A.

When the substrate 12A is inserted between the element electrode terminals 11e, each of the element electrode terminals 11e can be inserted into the notch portion 12c and the electrode terminal notch portion 12f of each of the electrode pads 12a of the substrate 12A and can be brought into contact with the insulating plate 12b exposed to the substrate pad notch portion 12c.

The substrate pad notch portions 12c are formed at positions corresponding to each other on the main surfaces on both sides of the substrate 12A.

When the substrate 12A is inserted between the element electrode terminals 11e, portions (front end portions) of the insulating plate 12b exposed to the substrate pad notch portion 12c at positions corresponding to each other on the main surfaces on both sides can be inserted between the element electrode terminals 11e. Thereby, the insulating plate 12b can be positioned in the height direction (Z direction) with respect to the imaging element 11A by the element electrode terminals 11e disposed on both sides in a thickness direction of the insulating plate 12b.

As a configuration of the insulating plate 12b of the substrate 12A inserted between the element electrode terminals 11e, both a configuration in which the insulating plate 12b is in contact with one or both of the element electrode terminals 11e on both sides in the thickness direction of the insulating plate 12b and another configuration in which the insulating plate 12b is not in contact with either of the element electrode terminals 11e on both sides can be employed.

The separation distance between the element electrode terminals 11e is set to be equal to or slightly larger than a plate thickness of the insulating plate 12b of the substrate 12A and is set so that the substrate 12A inserted between the element electrode terminals 11e can be positioned in the height direction with respect to the imaging element 11A.

Therefore, the substrate 12A inserted between the element electrode terminals 11e is positioned in the height direction with respect to the imaging element 11A irrespective of contact or separation of the insulating plate 12b of the substrate 12A with respect to the element electrode terminals 11e.

As shown in FIGS. 5A and 5B, when the positioning step is completed, the substrate 12A is disposed to be sandwiched between the element electrode terminals 11e in contact with the substrate electrode terminals 12e provided on one main surface of the substrate 12A and the element electrode terminals 11e in contact with the substrate electrode terminals 12e provided on the other main surface of the substrate 12A.

At this time, more specifically, the insulating plate 12b of the substrate 12A is disposed to be sandwiched between the element electrode terminals 11e which are respectively inserted into the notch portions 12c of the electrode pads 12a on both sides of the insulating plate 12b.

As a result, in the positioning step, positioning of the substrate 12A in the height direction (Z direction) with respect to the imaging element 11A can be easily and reliably performed simply by inserting the substrate 12A between the element electrode terminals 11e in contact with the substrate electrode terminals 12e provided on one main surface of the substrate 12A and the element electrode terminals 11e in contact with the substrate electrode terminals 12e provided on the other main surface of the substrate 12A.

In the positioning step, by inserting the substrate 12A between the element electrode terminals 11e, each of the element electrode terminals 11e is inserted into the notch portion 12c and the electrode terminal notch portion 12f of each of the electrode pads 12a of the substrate 12A, and the element electrode terminal 11e is brought into contact with the substrate electrode terminal 12e (specifically, an inner circumferential surface of the electrode terminal notch portion 12f).

Further, in the positioning step, portions (front end portions) of the insulating plate 12b of the substrate 12A exposed to the substrate pad notch portions 12c formed at positions corresponding to each other on the main surfaces on both sides are inserted between the element electrode terminals 11e.

As a result, in the positioning step, simply by inserting the front end portion of the substrate 12A between the element electrode terminals 11e and bringing the inner circumferential surfaces of the electrode terminal notch portions 12f into contact with the element electrode terminals 11e, positioning of the substrate 12A in the width direction, the front-rear direction, and the height direction with respect to the imaging element 11A can be easily and reliably performed by inserting the insulating plate 12b between the inner circumferential surface shape of the electrode terminal notch portion 12f and the element electrode terminal 11e.

In the positioning step, the substrate 12A is provided on the rear side of the imaging element 11A to extend rearward from the imaging element 11A.

Also, in the positioning step, the substrate 12A is held in a direction in which the substrate 12A extends from the rear surface 11b toward the rear side (a side opposite to the imaging surface 11a) with respect to the imaging element 11A using a support tool or the like.

When the positioning step is completed, while maintaining the position and orientation of the substrate 12A with respect to the imaging element 11A using a support tool or the like, the conductive connecting material portion 13 (see FIGS. 6A and 6B) is formed by performing the imaging element mounting step.

In the imaging element mounting step, the element electrode terminal 11e and the substrate electrode terminal 12e are heat-melted (reflowed) to be integrated, and then cooled and solidified to form the conductive connecting material portion 13.

When the imaging element mounting step is completed, electrical connection between the element electrode pad 11d and the substrate electrode pad 12a is reliably secured by the conductive connecting material portion 13, and the substrate 12A is supported in a direction in which the substrate 12 extends from the imaging element 11A toward the rear side with respect to the imaging element 11A by the conductive connecting material portion 13.

As a result, the imaging module 10A is assembled, and manufacture of the imaging module 10A is completed.

Connecting (electrical connecting) and fixedly joining a conductor 14a of an electric cable 14 to a rear end portion of the substrate electrode pad 12a can be performed as in the method of manufacturing the imaging module according to the first embodiment at the rear end portion of the substrate electrode pad 12a using a cable connection terminal formed of a thermally fusible conductive metal material or a conductive adhesive.

Figure 7:
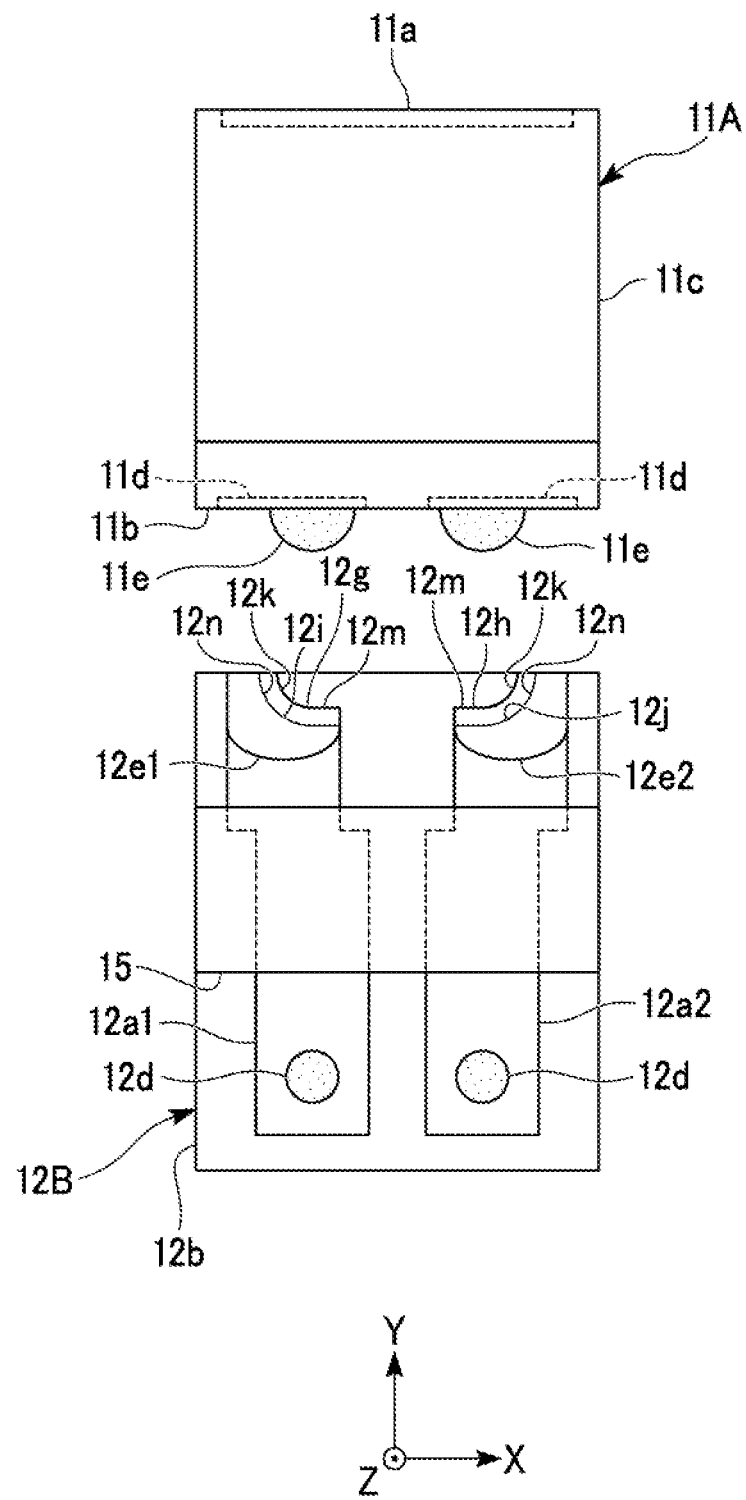
FIG. 7 is a plan view showing a modified example of the substrate used in the imaging module and the method of manufacturing the imaging module.
Figure 8:
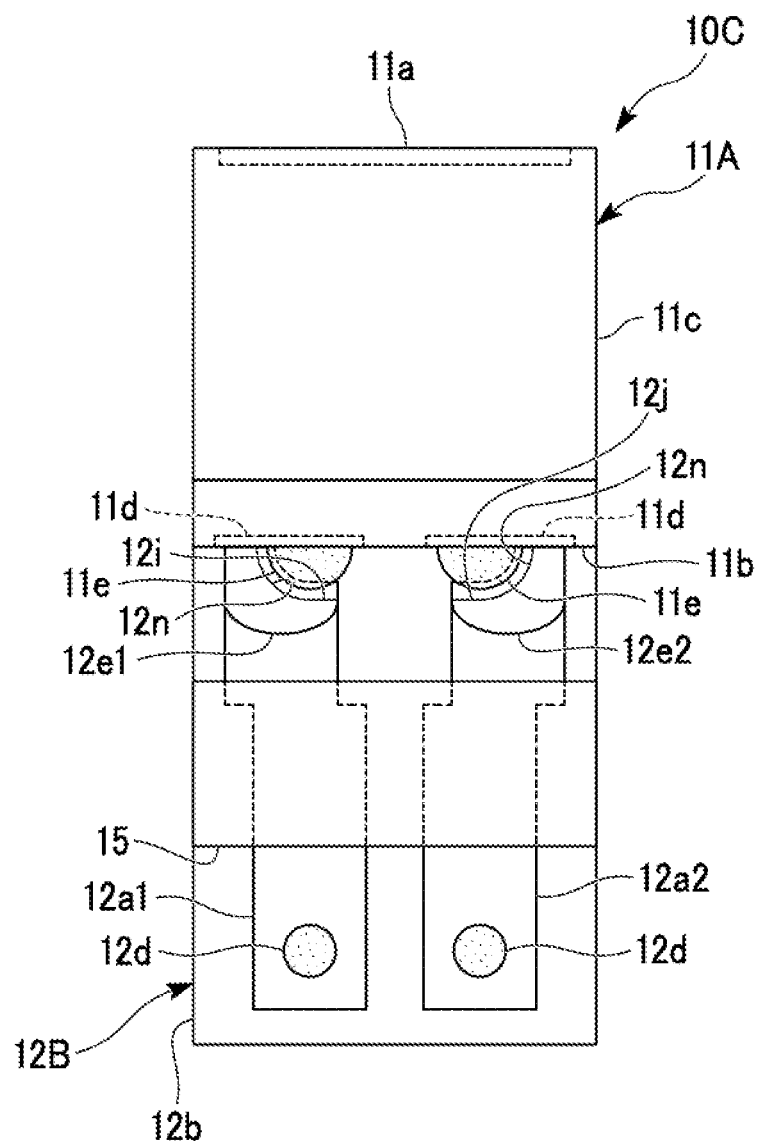
FIG. 8 is a plan view showing a state in which the electrode terminal of the substrate (substrate electrode terminal) is brought into contact with the element electrode terminal of the imaging element by the positioning step in a method of manufacturing the imaging module using the substrate shown in FIG. 7.
Figure 9:
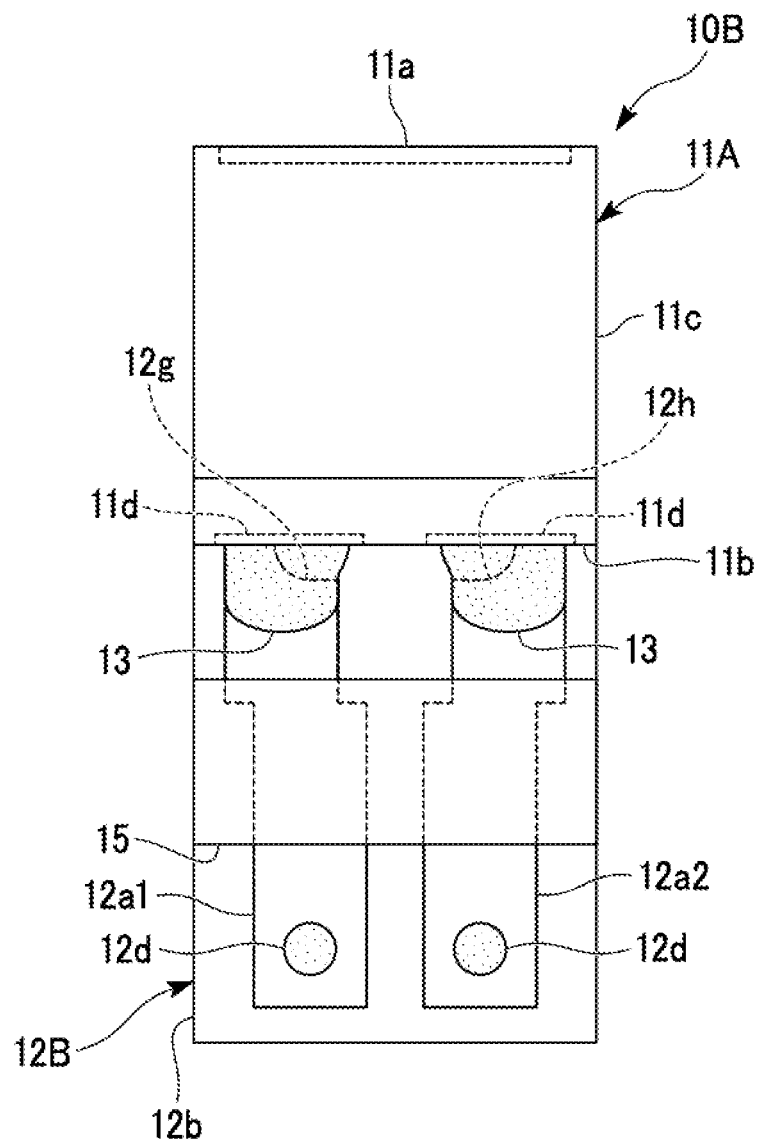
FIG. 9 is a plan view showing an imaging module assembled by performing the imaging element mounting step from the state shown in FIG. 8.

FIGS. 7, 8, and 9 show an example in which a substrate 12B of a modified example is used.

In FIGS. 7, 8, and 9, the same reference numerals are given to components the same as those in FIGS. 1 to 6, and a description thereof will be omitted or simplified.

A substrate 12B shown in FIG. 7 includes electrode pads 12a1 and 12a2 (substrate electrode pads) provided on main surfaces on both sides of the substrate 12B. The substrate 12B shown in FIG. 7 differs from the substrate 12A shown in FIGS. 4A and 4B in that the electrode pads 12a shown in FIGS. 4A and 4B are changed to the electrode pads 12a1 and 12a2 (substrate electrode pads) in which shapes of notch portions of front end portion are different.

As shown in FIG. 7, the substrate 12B includes a plurality (two in FIG. 7) of electrode pads 12a1 and 12a2 formed on the main surface to extend rearward from a front end of the substrate 12B.

In the main surface front end portion of the electrode pads 12a1 and 12a2 (portions positioned at the substrate front end portion on the main surface), notch portions 12g and 12h (substrate pad notch portions) are formed at the front end portions adjacent to each other.

The substrate pad notch portions 12g and 12h of the substrate 12B shown in FIG. 7 are formed in a shape recessed from portions of regions (ranges) including respective front ends (distal ends) facing each other at the front end portions of the electrode pads 12a1 and 12a2 (substrate electrode pads) adjacent to each other in the main surface front end portion.

The substrate pad notch portions 12g and 12h are respectively provided at portions facing each other in the front end portion of the substrate electrode pads 12a1 and 12a2, and are formed to be recessed rearward from the front end of the front end portion.

FIG. 7 shows the substrate 12B in a state before the imaging element 11A (the imaging element described in the second embodiment) is mounted on the substrate.

Thermally fusible substrate electrode terminals 12e1 and 12e2 are respectively provided at the front end portions of a pair of electrode pads 12a1 and 12a2 adjacent to each other in the substrate 12B in a state shown in FIG. 7.

Notch portions 12i and 12j (substrate electrode terminal notch portions) in an inner circumferential shape conforming to an inner circumferential surface of the substrate pad notch portions 12g and 12h are respectively formed in the substrate electrode terminals 12e1 and 12e2 (adjacent substrate electrode terminals) respectively formed at the front end portions of the pair of electrode pads 12a1 and 12a2 adjacent to each other.

The substrate pad notch portions 12g and 12h are respectively positioned at the front end portions of the electrode pads 12a1 and 12a2 (substrate electrode pads) adjacent to each other in the main surface front end portion, and are formed in a shape recessed from the portions of regions (ranges) including the front ends (distal ends) facing each other.

As a formation material of the substrate electrode terminals 12e1 and 12e2, a material that can be used for forming the substrate electrode terminal according to the first embodiment is employed.

FIG. 9 shows an imaging module 10B assembled by mounting the imaging element 11A shown in FIG. 7 on the substrate 12B.

Next, a method of assembling the imaging module 10B (a method of manufacturing the imaging module) using the imaging element 11A and the substrate 12B shown in FIG. 7 will be described. In this method, a positioning step (see FIG. 8) of positioning the substrate 12B with respect to the imaging element 11A by bringing the substrate electrode terminals 12e1 and 12e2 into contact with the element electrode terminals 11e, and after performing the positioning step, an imaging element mounting step in which the conductive connecting material portion 13 (see FIG. 9) is formed by heat-melting (reflowing) the substrate electrode terminals 12e1 and 12e2 and the element electrode terminals 11e and thereafter by cooling and solidifying the heat-melted portion while maintaining the positioning state of the substrate 12B with respect to the imaging element 11A, are performed.

The substrate 12B includes a pair of electrode pads 12a1 and 12a2 and substrate electrode terminals 12e1 and 12e2 shown in FIG. 7 on both sides (main surfaces on both sides) of the substrate 12B.

Further, the substrate electrode terminals 12e1 and 12e2 are formed at the front end portions of the electrode pads 12a1 and 12a2 by the same forming method as that for the substrate electrode terminal 12e exemplified in the first and second embodiments.

In the positioning step, the substrate 12B disposed on the rear side of the imaging element 11A is disposed to be oriented in a direction in which the substrate 12B extends rearward from the imaging element 11A. While maintaining an orientation of the substrate, the substrate is moved toward the imaging element rear surface 11b, the front end portion of the substrate 12B is inserted between the element electrode terminals 11e which are brought into contact with the substrate electrode terminals 12e1 and 12e2 on one main surface of the substrate 12B and the element electrode terminals 11e which are brought into contact with the substrate electrode terminals 12e1 and 12e2 on the other main surface of the substrate 12B, and thereby the substrate 12B is positioned in the height direction with respect to the imaging element 11A.

Further, in the positioning step, as shown in FIG. 8, as the substrate 12A moves toward the imaging element 11A, each of the element electrode terminals 11e is inserted into each of the notch portions 12i and 12j of the substrate electrode terminals 12e1 and 12e2 on each of the main surfaces of the substrate 12B, and the substrate electrode terminals 12e1 and 12e2 (specifically, the rear end portion inner circumferential surfaces of the notch portions 12i and 12j) are respectively brought into contact with the element electrode terminals 11e.

At the notch portions 12i and 12j (substrate electrode terminal notch portions) of the substrate electrode terminals 12e1 and 12e2 at the front end portions of the electrode pads 12a1 and 12a2 adjacent to each other in the main surface front end portion of the substrate 12A, the element electrode terminals 11e provided separately from each other on the imaging element 11 are inserted.

In the positioning step, by bringing the substrate electrode terminals 12e1 and 12e2 (specifically, the rear end portion inner circumferential surfaces of the notch portions 12i and 12j) into contact with the element electrode terminals 11e, the substrate 12B can be positioned in the front-rear direction and the width direction with respect to the imaging element 11A due to the inner circumferential surfaces of the electrode terminal notch portions 12i and 12j.

As shown in FIG. 7, each of the inner circumferential surfaces of the notch portions 12g and 12h positioned at the front end portions of the pair of the substrate electrode pads 12a1 and 12a2 adjacent to each other in the main surface front end portion of the substrate 12A includes an inner side surface portion 12k and a rear end inner surface portion 12m. The inner side surface portion 12k has a curve line extending in a direction from each of the front ends of the substrate electrode pads 12a1 and 12a2 toward a rear side to approach the facing substrate electrode pad and is formed to be curved. In other words, the inner side surface portion 12k positioned at the front end portion of the substrate electrode pad 12a1 has a curve line extending in a direction from the front end of the substrate electrode pad 12a1 toward the rear side to approach the front end portion of the substrate electrode pad 12a2. Similarly, the inner side surface portion 12k positioned at the front end portion of the substrate electrode pad 12a2 has a curve line extending in a direction from the front end of the substrate electrode pad 12a2 toward the rear side to approach the front end portion of the substrate electrode pad 12a1. The rear end inner surface portion 12m of each of the substrate electrode pads 12a1 and 12a2 extends from a rear end in the front-rear direction of the inner side surface portion 12k along the width direction of the substrate electrode pad.

In the front end portion of the substrate electrode pad, the rear end inner surface portion 12m is formed to extend from a side surface facing a region between the front end portions of the pair of substrate electrode pads 12a1 and 12a2 to the rear end of the inner side surface portion 12k.

The notch portions 12i and 12j of the pair of substrate electrode terminals 12e1 and 12e2 adjacent to each other in the main surface front end portion of the substrate 12A are respectively formed in a shape conforming to the inner circumferential surfaces of the substrate pad notch portions 12g and 12h in the substrate electrode terminals 12e1 and 12e2.

The substrate electrode terminal notch portions 12i and 12j are respectively formed in a shape recessed from portions facing each other in a region (range) including respective front ends.

The inner circumferential surfaces of the substrate electrode terminal notch portions 12i and 12j are formed to rise from an end on surface sides of the substrate electrode pads 12a1 and 12a2 (a side opposite to the insulating plate 12b) at the inner circumferential surfaces of the substrate pad notch portions 12g and 12h toward a side opposite to the insulating plate 12b.

The inner circumferential surface of each of the substrate electrode terminal notch portions 12i and 12j has an inner side surface portion 12n along the inner side surface portion 12k of each of the substrate pad notch portions 12g and 12h.

However, the inner side surface portion 12n of each of the substrate electrode terminal notch portions 12i and 12j is formed into a tapered shape in which a diameter thereof increases with distance away from the inner side surface portion 12k of each of the substrate pad notch portions 12g and 12h in the height direction.

In the positioning step, two element electrode terminals 11e which are respectively brought into contact with the substrate electrode terminals 12e1 and 12e2 adjacent to each other as the substrate 12B moves toward the rear surface 11b of the imaging element 11A are inserted between the inner side surface portions 12n of the notch portions 12i and 12j of the adjacent substrate electrode terminals 12e1 and 12e2, and are respectively brought into contact with the inner circumferential surface rear end portions of the substrate electrode terminal notch portions 12i and 12j.

Each of the element electrode terminals 11e is brought into contact with the rear end portion of the inner side surface portion 12n of each of the substrate electrode terminal notch portions 12i and 12j, or brought into contact with a portion along the rear end inner surface portion 12m of each of the substrate pad notch portions 12g and 12h on the inner circumferential surface of each of the substrate electrode terminal notch portions 12i and 12j.

In consideration of sizes of the two element electrode terminals 11e and a separation distance between the two element electrode terminals 11e which are respectively brought into contact with the adjacent substrate electrode terminals 12e1 and 12e2, the notch portions 12i and 12j of the adjacent substrate electrode terminals 12e1 and 12e2 are formed so that the two element electrode terminals 11e can be inserted between the inner side surface portion 12n of each of the notch portions 12i and 12j and can be respectively brought into contact with the inner circumferential surface rear end portions of the notch portions 12i and 12j.

By bringing the inner circumferential surface rear end portions of the notch portions 12i and 12j respectively into contact with the element electrode terminals 11e, the adjacent substrate electrode terminals 12e1 and 12e2 serve the role of positioning the substrate 12B in the front-rear direction (Y direction) with respect to the imaging element 11A.

Further, when the element electrode terminals 11e are respectively brought into contact with the inner circumferential surface rear end portions of the substrate electrode terminal notch portions 12i and 12j, the inner side surface portions 12n of the notch portions 12i and 12j of the adjacent substrate electrode terminals 12e1 and 12e2 are respectively brought into contact with the element electrode terminals 11e or disposed close to the element electrode terminals 11e with a slight clearance therebetween.

Only one side of the inner side surface portion 12n of each of the notch portions 12i and 12j of the adjacent substrate electrode terminals 12e1 and 12e2 may be in contact with the element electrode terminal 11e and the other side thereof may be disposed close to the element electrode terminal 11e without being in contact therewith.

The notch portions 12i and 12j of the adjacent substrate electrode terminals 12e1 and 12e2 position the substrate 12B in the width direction (X direction) with respect to the imaging element 11A (specifically, the element electrode terminals 11e) while securing required positioning accuracy by the respective inner side surface portions 12n.

When the positioning step is completed, an imaging element mounting step is performed.

In the imaging element mounting step, the substrate electrode terminals 12e1 and 12e2 and the element electrode terminals 11e which are brought into contact with each other are heat-melted (reflowed) and then cooled and solidified to form the conductive connecting material portion 13 shown in FIG. 8, and thereby electrically connecting and fixedly joining the substrate electrode pads 12a1 and 12a2 to the element electrode pads 11d is realized.

As a result, the imaging module 10B having the configuration in which the imaging element 11A is mounted on the substrate 12B is obtained.

Further, the inner side surface portions of the inner circumferential surfaces of the substrate pad notch portions 12g and 12h are not limited to the curved surface shown in FIG. 7, and may employ, for example, a shape formed to extend in a straight line from the front ends of the substrate electrode pads 12a1 and 12a2 to approach the other side of the adjacent substrate electrode pads toward the rear side.

In the inner circumferential surfaces of the substrate pad notch portions 12g and 12h, when the inner side surface portion thereof is, for example, a curved surface or a surface formed to extend in a straight line from the front ends of the substrate electrode pads 12a1 and 12a2 to approach the other side of the adjacent substrate electrode pads toward the rear side, the inner circumferential surfaces of the substrate pad notch portions 12g and 12h are not necessarily required to have the rear end inner surface portion and a configuration without the rear end inner surface portion can be employed.

Further, the inner side surface portions of the inner circumferential surfaces of the substrate pad notch portions 12g and 12h may be formed to extend in a straight line in the front-rear direction.

In this case, a configuration in which the inner circumferential surfaces of the substrate pad notch portions 12g and 12h respectively have the rear end inner surface portions is employed.

The substrate electrode terminal notch portions 12*i* and 12*j* are formed into a shape having an inner circumferential surface conforming to the inner circumferential surface of the substrate pad notch portions 12*g* and 12*h*.

When the inner circumferential surfaces of the substrate pad notch portions 12*g* and 12*h* have the rear end inner surface portions, the substrate electrode terminal notch portions 12*i* and 12*j* respectively have portions conforming to the rear end inner surface portions of the substrate pad notch portions 12*g* and 12*h*.

The semicircular notch portion 12*f* of each of the substrate electrode terminals 12*e* of the substrates 12 and 12A according to the first and second embodiments is formed such that the substrate can be positioned in the width direction (X direction) with respect to the element electrode terminal while securing a preset required accuracy by bringing the inner circumferential surface rear end portion into contact with the element electrode terminal.

On the other hand, for example, as shown in FIG. 7, the substrate electrode terminals 12*e*1 and 12*e*2 adjacent to each other in the substrate main surface front end portion position the substrate in the width direction (X direction) with respect to the element electrode terminals 11*e* while securing preset required positioning accuracy by accommodating the element electrode terminals 11*e* to be brought into contact with the respective substrate electrode terminals 12*e*1 and 12*e*2 between the inner side surface portions 12*k* of the notch portions 12*i* and 12*j*.

The notch portions 12*i* and 12*j* of the adjacent substrate electrode terminals 12*e*1 and 12*e*2 each have a shape recessed from portions facing each other in a region (range) including respective front ends, and are simple in shape compared to the notch portions 12*f* of the substrate electrode terminals of the substrates 12 and 12A according to the first and second embodiments, and thus it is easy to secure formation thereof and formation accuracy.

Figure 10A:
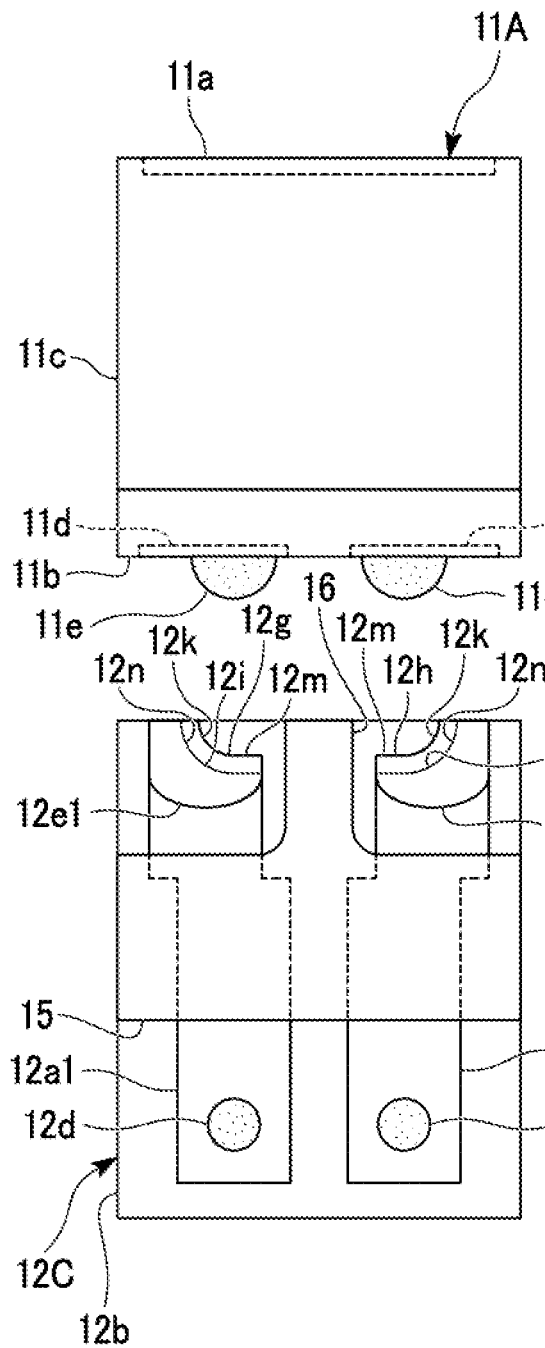
FIG. 10A is a plan view showing a substrate having a configuration in which an inter-electrode pad insulating wall portion is provided between adjacent front end portions of a plurality of electrode pads (substrate electrode pads) provided on the substrate shown in FIG. 7.
Figure 10B:
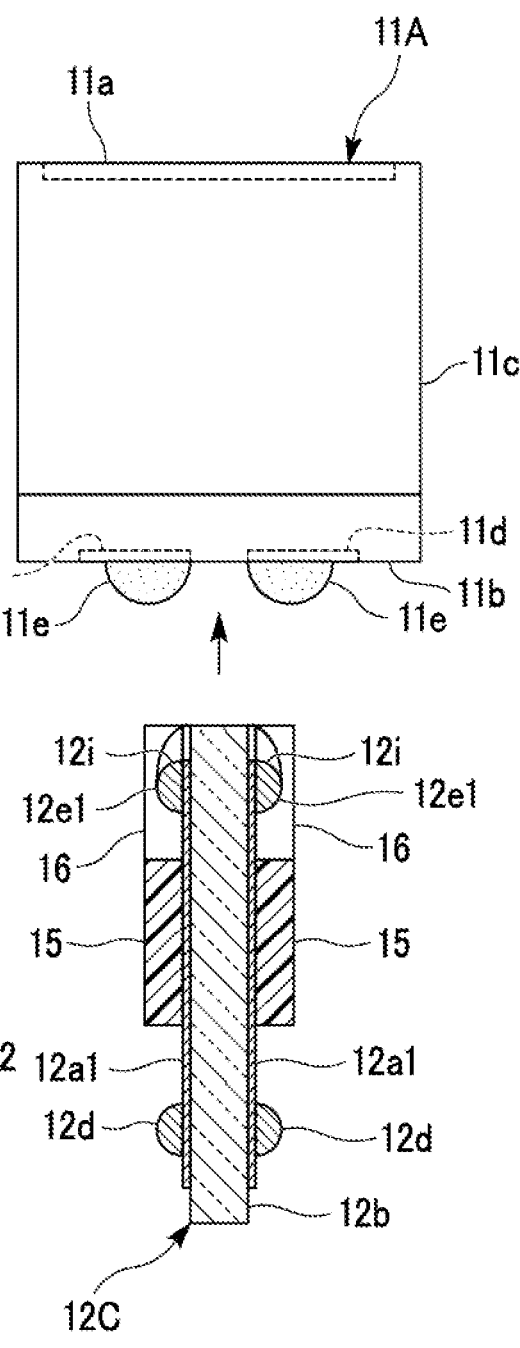
FIG. 10B is a side view showing the substrate having a configuration in which the inter-electrode pad insulating wall portion is provided between adjacent front end portions of a plurality of electrode pads (substrate electrode pads) provided on the substrate shown in FIG. 7.

As shown in FIGS. 10A and 10B, as a configuration of the substrate, it is also possible to employ a configuration in which an electrically insulating inter-pad insulating wall portion 16 is provided between the front end portions of the electrode pads 12*a*1, 12*a*2 adjacent to each other at the main surface front end portion of the substrate.

Figure 11:
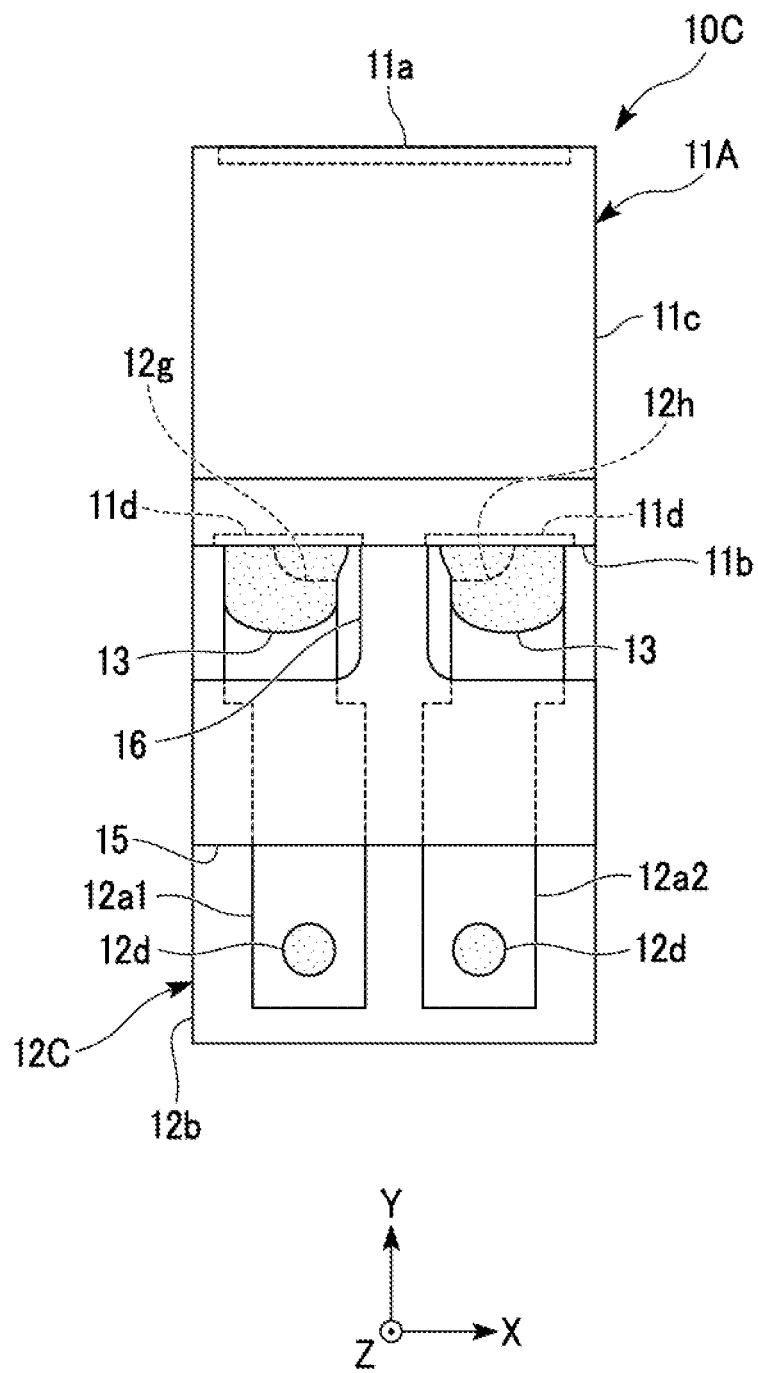
FIG. 11 is a plan view showing an imaging module assembled by mounting an imaging element on the substrate shown in FIG. 10.

A reference numeral 12C is added to a substrate shown in FIGS. 10A and 10B, and a reference numeral 10C is added to an imaging module of FIG. 11 assembled using the substrate 12C.

The substrate 12C shown in FIGS. 10A and 10B has a structure in which the inter-pad insulating wall portion 16 is provided between the front end portions of the electrode pads 12*a*1 and 12*a*2 adjacent to each other at the main surface front end portion of the substrate 12B shown in FIGS. 7 and 8.

The inter-pad insulating wall portion 16 is formed to protrude in a rib shape extending in the front-rear direction at the main surface front end portion of the insulating plate 12*b*.

The inter-pad insulating wall portion 16 is formed at the front end portions of the main surfaces on both sides of the insulating plate 12*b*.

However, it is also possible to employ a configuration in which the inter-pad insulating wall portion 16 is formed on the front end portion of only one main surface of both sides of the insulating plate 12*b* as the substrate 12C.

The inter-pad insulating wall portion 16 is formed of an electrically insulating material such as a resin.

The inter-pad insulating wall portion 16 may be formed, for example, by a resin layer provided on the main surface of the insulating plate 12*b*, by a protruding portion in which a portion of the insulating plate 12*b* protrudes toward the main surface of the insulating plate 12*b*, or the like.

The inter-pad insulating wall portion 16 prevents a short circuit from occurring between the substrate electrode pads 12*a* or the like due to a flow of the formation material of the element electrode terminal 11*e* and the substrate electrode terminal 12*e* which are heat-melted in the imaging element mounting step.

Further, the inter-pad insulating wall portion 16 shown in FIGS. 10A and 10B is formed to extend from the front-rear insulating wall portion 15 of the substrate 12C toward a front side of the substrate 12C.

However, the inter-pad insulating wall portion 16 may be a rib-shaped protruding portion formed on the main surface of the substrate 12C (the main surface of the insulating plate 12*b*) separately from the front-rear insulating wall portion 15.

As shapes of the notch portions 12*i* and 12*j* and the substrate electrode terminals 12*e*1 and 12*e*2 which are positioned at the front end portions of the substrate electrode pads 12*a*1 and 12*a*2 adjacent to each other shown in FIG. 7, and the configuration of the inter-pad insulating wall portion 16 shown in FIGS. 10A and 10B, the invention is not limited only to the substrate configuration having the substrate electrode pads and the substrate electrode terminals on the main surfaces on both sides, and a substrate configuration having the substrate electrode pads and the substrate electrode terminals on only one main surface is also applicable.

Figure 12A:
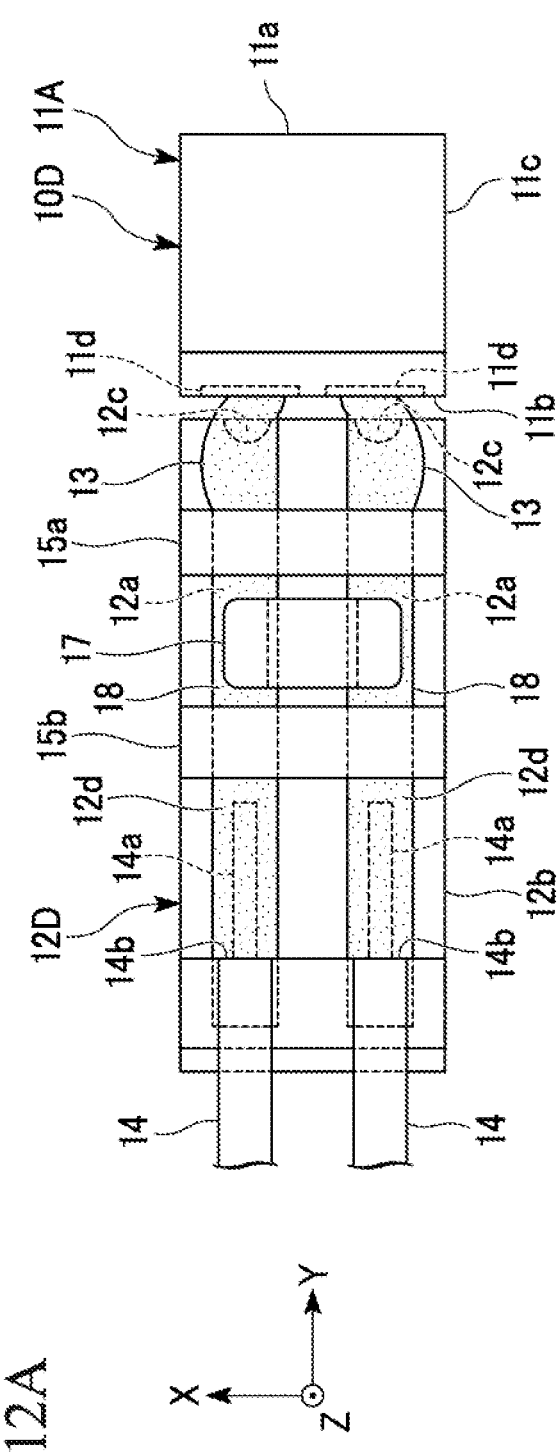
FIG. 12A is a plan view showing an imaging module having a configuration in which electronic component connection terminals are provided on electrode pads (substrate electrode pads) provided on the substrate of the imaging module shown in FIGS. 6A and 6B.
Figure 12B:
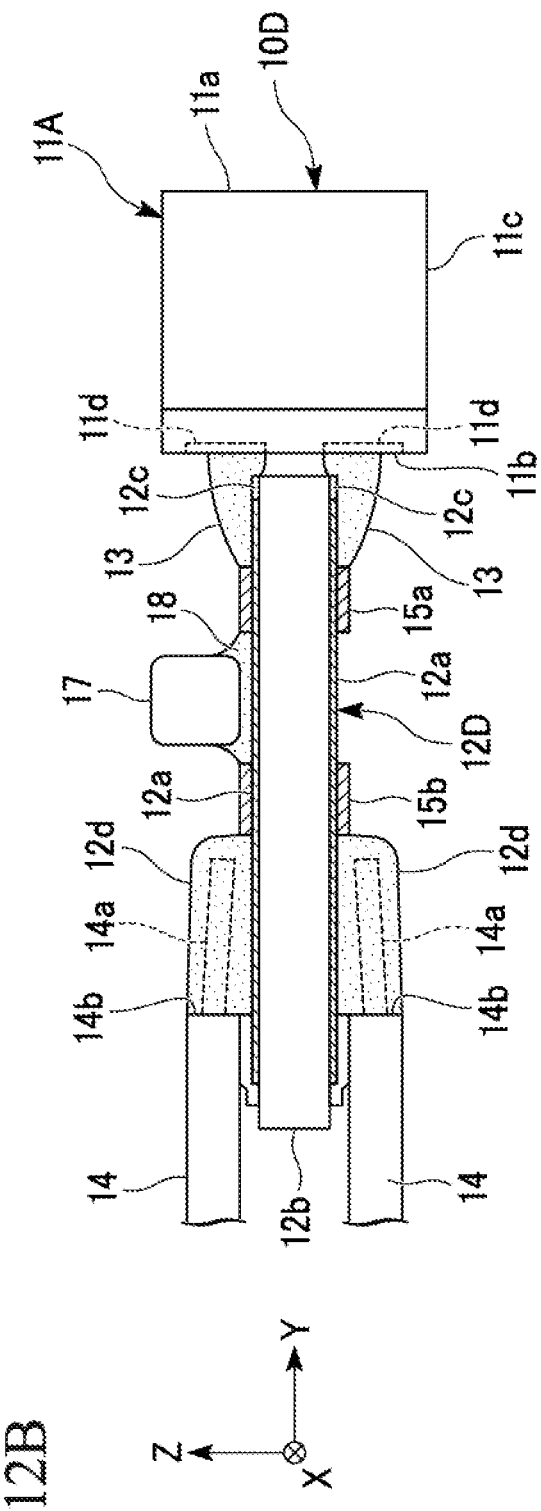
FIG. 12B is a side view showing the imaging module having the configuration in which the electronic component connection terminals are provided on the electrode pads (substrate electrode pads) provided on the substrate of the imaging module shown in FIGS. 6A and 6B.

As shown in FIGS. 12A and 12B, the substrate may also employ a configuration in which the substrate includes a thermally fusible electronic component connection terminal 18 for electrically connecting and mounting the electronic component 17 to the substrate electrode pad 12*a* at a central portion in the front-rear direction of the substrate electrode pad 12*a* between the front end portion thereof electrically connected to the element electrode pad 11*d* via the conductive connecting material portion 13 and the rear end portion thereof to which the conductor 14*a* of the electric cable 14 is electrically connected.

The electronic component connection terminal 18 is formed using a formation material that can be employed for the conductive connecting material portion 13 such as solder, for example.

The electronic component 17 is, for example, a resistive element, a chip capacitor, a diode, or the like.

Further, a clearance secured between a front end portion of a substrate 12D and an imaging element rear surface 11*b* is clearly shown in FIGS. 12A and 12B.

The substrate 12D shown in FIGS. 12A and 12B has the electronic component connection terminal 18 only on the substrate electrode pad 12*a* on the main surface on one side.

However, for the substrate 12D, it is also possible to employ a configuration in which the electronic component connection terminal 18 is provided at the central portion in the front-rear direction of the substrate electrode pad 12*a* on the main surfaces on both sides of the substrate 12D.

FIGS. 12A and 12B show the substrate 12D and the imaging module 10D having a configuration in which the electronic component connection terminal 18 is electrically connected and mounted on the substrate electrode pad 12*a* only on one main surface of the substrate 12A of the imaging module 10A shown in FIGS. 6A and 6I.

The front end portion of the substrate electrode pad 12*a* included in the substrate 12D of the imaging module 10D shown in FIGS. 12A and 12B is fixedly joined to the imaging element electrode pad 11d and electrically connected thereto via the conductive connecting material portion 13.

The conductor 14a of the electric cable 14 is fixedly joined and electrically connected to the rear end portion of the substrate electrode pad 12a by the same cable connection terminal 12d (thermally fusible conductive metal material in FIGS. 12A and 12B) described in the imaging module and the method of manufacturing the same according to the second embodiment.

The electronic component 17 is fixedly joined and electrically connected to the central portion in the front-rear direction of the substrate electrode pads 12a by the electronic component connection terminal 18 (thermally fusible conductive metal material in FIGS. 12A and 12B).

In addition, front-rear insulating wall portions 15a and 15b (a front-side front-rear insulating wall portions 15a, and a rear-side front-rear insulating wall portions 15b) are provided to be spaced apart from each other in the front-rear direction on the main surfaces on both sides of the substrate 12D of the imaging module 10D shown in FIGS. 12A and 12B.

The front-rear insulating wall portions 15a and 15b are electrically insulating protruding walls formed of a formation material that can be used for forming the front-rear insulating wall portion 15 shown in FIGS. 2A and 2B on the main surface of the insulating plate 12b.

As shown in FIGS. 12A and 12B, the front-rear insulating wall portions 15a and 15b each extend in a width direction thereof on the main surface of the insulating plate 12b and cover a portion in an extending direction of the substrate electrode pads 12a.

On the main surface on which the electronic component connection terminal 18 of the substrate 12D shown in FIGS. 12A and 12B is provided, the front-side front-rear insulating wall portion 15a is formed between the conductive connecting material portion 13 and the electronic component connection terminal 18. The rear-side front-rear insulating wall portion 15b is formed between the electronic component connection terminal 18 and the cable connection terminal 12d.

The front-side front-rear insulating wall portion 15a and the rear-side front-rear insulating wall portion 15b on a main surface positioned on a side opposite to the portion of the substrate 12D in which the electronic component connection terminal 18 is provided are provided at positions corresponding to the front-side front-rear insulating wall portion 15a and the rear-side front-rear insulating wall portion 15b in the portion in which the electronic component connection terminal 18 is provided.

Using a substrate having a configuration in which the electronic component connection terminal 18, the front-side front-rear insulating wall portion 15a, and the rear-side front-rear insulating wall portion 15b are provided on the substrate 12A shown in FIGS. 4A and 4B, the imaging module 10D shown in FIGS. 12A and 12B is obtained by mounting and assembling the imaging element 11A on the substrate.

Manufacture of the imaging module 10D using the substrate and the imaging element 11A can be realized by performing a positioning step first and then performing an imaging element mounting step as in the method of manufacturing the imaging module according to the second embodiment.

The electronic component connection terminal 18 is formed in a layered form or hemispherical shape by overlaying a formation material thereof on the central portion in the front-rear direction of the substrate electrode pad 12a of the substrate.

In a substrate in a state before the imaging element 11A is mounted on the substrate, the front-side front-rear insulating wall portion 15a is positioned between the substrate electrode terminal 12e and the electronic component connection terminal 18, and the rear-side front-rear insulating wall portion 15b is positioned between the electronic component connection terminal 18 and the cable connection terminal 12d.

When the substrate electrode terminal 12e and the element electrode terminal 11e with which the substrate electrode terminal 12e is brought into contact are heat-melted, the front-side front-rear insulating wall portion 15a prevents a formation material (formation material of the conductive connecting material portion 13) of the substrate electrode terminal 12e and the element electrode terminal 11e which are heat-melted from reaching the electronic component connection terminal 18 due to the flow thereof.

The front-side front-rear insulating wall portion 15a can prevent the formation material of the conductive connecting material portion 13 in a heat-melted state from reaching the electronic component connection terminal 18 and causing the electronic component connection terminal 18 to affect electrical connection between the electronic component 17 and the substrate electrode pad 12a.

The rear-side front-rear insulating wall portion 15b prevents the formation material of the thermally fusible cable connection terminal 12d heat-melted for electrically connecting the conductor 14a of the electric cable 14 to the rear end portion of the substrate electrode pad 12a from reaching the electronic component connection terminal 18 due to the flow thereof.

The rear-side front-rear insulating wall portion 15b can prevent the formation material of the cable connection terminal 12d in a heat-melted state from reaching the electronic component connection terminal 18 and causing the electronic component connection terminal 18 to affect electrical connection between the electronic component 17 and the substrate electrode pad 12a.

Further, it is also possible to employ a configuration in which the front-side front-rear insulating wall portion 15a and the rear-side front-rear insulating wall portion 15b are not provided on the substrate.

However, the substrate having the front-side front-rear insulating wall portion 15a and the rear-side front-rear insulating wall portion 15b (the substrate in a state before the imaging element is mounted) can have a shorter distance between the substrate electrode terminal 12e and the electronic component connection terminal 18 and a shorter distance between the cable connection terminal 12d and the electronic component connection terminal 18 as compared with a configuration in which the front-side front-rear insulating wall portion 15a and the rear-side front-rear insulating wall portion 15b are not provided.

Therefore, the substrate having the front-side front-rear insulating wall portion 15a and the rear-side front-rear insulating wall portion 15b (the substrate in a state before the imaging element is mounted) is advantageous for downsizing the substrate itself and the entire imaging module.

As shown in FIGS. 13A and 13B, in order to enable connection of a coaxial cable 14A (electric cable), the substrate can employ a configuration having an electrode pad 12o1 (hereinafter also referred to as an internal conductor electrode pad) to which an internal conductor 14c of the coaxial cable 14A is connected and an electrode pad 12o2

(hereinafter also referred to as an external conductor electrode pad) to which an external conductor 14d of the coaxial cable 14A is connected on the main surface of the substrate.

In a structure of an imaging module 10I shown in FIGS. 13A and 13B, the substrate 12A of the imaging module 10A shown in FIGS. 6A and 6B is changed to a substrate 12E having a configuration in which the internal conductor electrode pad 12o1 and the external conductor electrode pad 12o2 are provided on the main surface.

The substrate 12E shown in FIGS. 13A and 13B has an insulating plate 12b similar to that in the substrate 12A of the imaging module 10A shown in FIGS. 6A and 6B.

Structures on both sides of the substrate 12E with the insulating plate 12b interposed therebetween are the same.

The internal conductor electrode pad 12o1 and the external conductor electrode pad 12o2 are formed on the main surfaces on both sides of the substrate 12E (main surfaces on both sides of the insulating plate 12b).

Further, a clearance secured between a front end portion of the substrate 12E and the imaging element rear surface 11b is clearly shown in FIGS. 13A and 13B.

The electrode pads 12o1 and 12o2 of the substrate 12E shown in FIGS. 13A and 13B have front end portions similar in configuration to the front end portions of the electrode pads 12a of the substrate 12A of the imaging module 10 A shown in FIGS. 6A and 6B.

In the imaging module 10E shown in FIGS. 13A and 13B, the front end portions of the electrode pads 12o1 and 12o2 are electrically connected to the electrode pads 11d of the imaging element 11A via the conductive connecting material portion 13.

The internal conductor 14c of the coaxial cable 14A is fixedly joined and electrically connected to a rear end portion of the internal conductor electrode pad 12o1 by a cable conductor joining material 12d1.

The external conductor 14d of the coaxial cable 14A is fixedly joined and electrically connected to a rear end portion of the external conductor electrode pad 12o2 by a cable conductor joining material 12d2.

Hereinafter, the cable conductor joining material 12d1 for connecting the internal conductor 14c of the coaxial cable 14A to the rear end portion of the internal conductor electrode pad 12o1 is also referred to as an internal conductor joining material, and the cable conductor joining material 1242 for connecting the external conductor 14d of the coaxial cable 14A to the rear end portion of the external conductor electrode pad 12o2 is also referred to as an external conductor joining material.

As a formation material of the cable conductor joining materials 12d1 and 12d2, for example, a conductive bonding material including a material obtained by heating and solidifying a paste-like conductive bonding material (heat-solidification type conductive bonding material) that exhibits a bonding force due to heating and solidification, for example, such as a solder paste and a conductive adhesive (a material in which a filler such as a conductive metal such as silver is dispersed in a resin binder), a conductive metal material (solder or the like) that can be used for forming the cable connection terminal 12d of the imaging module 10A shown in FIGS. 6A and 6B, or the like can be employed.

The internal conductor electrode pad 12o1 shown in FIG. 13A is formed to extend in a straight line in the front-rear direction.

On the other hand, the external conductor electrode pad 12o2 includes bent portions 12p and 12q between the front end portion and the rear end portion thereof.

The rear end portion of the external conductor electrode pad 12o2 is provided at a position spaced rearward from the rear end portion of the internal conductor electrode pad 12o1.

The external conductor 14d of the coaxial cable 14 electrically connecting the internal conductor 14c to the rear end portion of the internal conductor electrode pad 12o1 can be electrically connected to the rear end portion of the external conductor electrode pad 12o2.

The imaging module 10E shown in FIGS. 13A and 13B has a configuration in which the external conductor 14d of the coaxial cable 14 electrically connecting the internal conductor 14c to the rear end portion of the internal conductor electrode pad 12o1 of the substrate 12E is electrically connected to the rear end portion of the external conductor electrode pad 12o2 to connect the coaxial cable 14 to the substrate 12E.

In the imaging module 10E shown in FIGS. 13A and 13B, the external conductor 14d of the coaxial cable 14 is connected to the imaging element 11A as its power supply line via the external conductor electrode pad 12o2.

The substrate 12E of the imaging module 10E shown in FIGS. 13A and 13B includes front-rear insulating wall portions 19a and 19b formed to be spaced apart from each other in the front-rear direction of the main surface of the substrate 12E (a front-side front-rear insulating wall portion 19a, a rear-side front-rear insulating portions wall portion 19b).

The front-side front-rear insulating wall portion 19a is formed between the conductive connecting material portions 13 and the rear end portion of the internal conductor electrode pad 12o1, in which the conductive connecting material portions 13 are respectively formed between the front end portions of the electrode pads 12o1 and 12o2 (substrate electrode pads) and the element electrode pads 11d.

The rear-side front-rear insulating wall portion 19b is formed between the rear end of the internal conductor electrode pad 12o1 and the external conductor electrode pad 12o2.

The front-side front-rear insulating wall portion 19a and the rear-side front-rear insulating wall portion 19b are electrically insulating protruding walls formed of a formation material that can be used for forming the front-rear insulating wall portion 15 shown in FIGS. 2A and 2 B on the main surface of the insulating plate 12b.

As shown in FIGS. 13A and 13B, the front-rear insulating wall portions 19a and 19b are each formed to extend in a width direction thereof on the main surface of the insulating plate 12b.

The front-side front-rear insulating wall portion 19a is formed to cover a portion in an extending direction of the electrode pads 12o1 and 12o2 for the internal conductor and the external conductor.

The rear-side front-rear insulating wall portion 19b is formed to cover a portion in an extending direction of the external conductor electrode pad 12o2.

The front-side front-rear insulating wall portion 19a limits expansion in the substrate front-rear direction of the formation material of the conductive connecting material portions 13 in a heat-melted state between the front-side front-rear insulating wall portion 19a and the imaging element electrode pads 11d, and effectively contributes to forming the conductive connecting material portions 13 into a desired shape (particularly securing a thickness of the conductive connecting material portions 13) between the front-side front-rear insulating wall portion 19a and the imaging element electrode pads 11d.

In addition, the front-side front-rear insulating wall portion 19a limits expansion in a front direction of the internal conductor joining material 12d1 connecting the internal conductor 14c of the coaxial cable 14A to the rear end portion of the internal conductor electrode pad 12o1, and thereby also serves the role of preventing the cable conductor joining material 12d1 from reaching the rear surface 11b of the imaging element 11A.

The rear-side front-rear insulating wall portion 19b serves the role of preventing contact between the internal conductor joining material 12d1 and the external conductor joining material 12d2 connecting the external conductor 14d of the coaxial cable 14A to the rear end portion of the external conductor electrode pad 12o2.

While the invention has been described on the basis of preferred embodiments, the disclosure is not limited to the preferred embodiments described above, and various modifications can be made without departing from the gist of the disclosure.

For example, configurations on both sides of the insulating plate of the substrate having electrode pads (substrate electrode pads) on the main surfaces on both sides (main surfaces on both sides of the insulating plate) are not limited to being the same configuration as each other, and may be different from each other.

Configurations of the substrate main surface such as shapes of the substrate electrode pads shown in FIGS. 7, 10A, 12A and 13A can also be applied to a substrate having electrode pads (substrate electrode pads) only on one main surface.

Connection between the front end portion of the substrate electrode pad and the electrode pad of the imaging element (element electrode pad) is not limited to the conductive connecting material portion 13, and it is also possible to employ a configuration in which an element electrode terminal formed to protrude from the element electrode pad using a conductive metal and the front end portion of the substrate electrode pad are fixedly joined using a paste-like conductive bonding material that exhibits a bonding force due to heating and solidification (including sintering) such as a solder paste and a conductive adhesive (a material in which a filler such as a conductive metal such as silver is dispersed in a resin binder).

The paste-like conductive bonding material that exhibits a bonding force due to heating and solidification (including sintering) is also referred to as a heat-solidification type conductive bonding material hereinafter.

In a case of using the heat-solidification type conductive bonding material, in a positioning step in a method of manufacturing the imaging module, a substrate electrode terminal formed by molding the heat-solidification type conductive bonding material is provided at the front end portion of the substrate electrode pad, brought into contact with the element electrode terminal, and thereby a substrate is positioned on the imaging element.

In an imaging element mounting step, the substrate electrode terminal in contact with the element electrode terminal is heated and solidified, and the element electrode terminal and the front end portion of the substrate electrode pad are fixedly joined and electrically connected by a bonding force of a formation material of the substrate electrode terminal (heated and solidified substance from heat-solidification type conductive bonding material).

Connection between the front end portion of the substrate electrode pad and the electrode pad of the imaging element is realized by using a conductive bonding material such as the conductive connecting material portion 13 made of a conductive metal material or a heat-solidification type conductive bonding material.

Also for the electronic component connection terminal and the cable connection terminal which are provided on the substrate electrode pad, a material formed of a conductive bonding material can be used.

In addition, the substrate can employ a configuration in which installation of the electronic component connection terminal and the cable connection terminal on the substrate electrode pad is omitted.

Further, even in the configuration in which installation of the electronic component connection terminal and the cable connection terminal on the substrate electrode pad is omitted, it is possible to realize fixedly joining and electrically connecting the conductors of the electric cable or the electronic components to the substrate electrode pad using the heat-solidification type conductive bonding material.

While preferred embodiments of the invention have been described and shown above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An imaging module comprising:
an imaging element that has an imaging surface and a rear surface opposite to the imaging surface, and includes element electrode pads provided on the rear surface, the element electrode pads extending in a first direction;
a substrate that is positioned on the rear surface of the imaging element, is provided to extend from the rear surface to a side opposite to the imaging surface, has an end face facing the rear surface of the imaging element, and has a main surface including a substrate electrode pad provided thereon, the substrate extending in a second direction intersecting with the first direction, the substrate electrode pad having a front end portion, the front end portion having a notch portion and an end formed by the notch portion, the end being located away from the end face of the substrate; and
a conductive connecting material portion that electrically connects the element electrode pads and the front end portion of the substrate electrode pad, wherein
the notch portion is formed at the front end portion of the substrate electrode pad so as to cause the main surface of the substrate to remain at the notch portion such that the main surface located at the front end portion is exposed through the notch portion and contacts the conductive connecting material portion.

2. The imaging module according to claim 1, wherein
the imaging element includes the element electrode pads on both sides of the rear surface with the front end portion of the substrate at a position close to the imaging element interposed therebetween, and
the front end portions of the substrate electrode pads each provided on main surfaces on both sides of the substrate are electrically connected to the element electrode pads of the imaging element via the conductive connecting material portions, respectively.

3. The imaging module according to claim 1, further comprising an electrically insulating inter-pad insulating wall portion provided between the substrate electrode pads adjacent to each other at the front end portion of the main surface of the substrate.

4. The imaging module according to claim 1, wherein the notch portions of the substrate electrode pads adjacent to each other at the front end portion of the main surface of the substrate are formed in a shape recessed from portions facing each other at regions including distal ends of the adjacent substrate electrode pads.

5. The imaging module according to claim 1, wherein the substrate includes:
a cable connection terminal provided on the substrate electrode pad to be spaced rearward from the notch portion; and
an electronic component connection terminal provided at a position between the conductive connecting material portion of the substrate electrode pad and the cable connection terminal.

6. The imaging module according to claim 1, wherein at the notch portion, the underlying main surface is exposed through the notch portion.

7. The imaging module according to claim 1, wherein at the notch portion, the exposed main surface extends from recessed bottom of the notch portion toward the rear surface of the imaging element.

8. The imaging module according to claim 1, wherein the notch portion has a curved shape.

9. The imaging module according to claim 1, further comprising an electric cable connected to a position spaced rearward from the notch portion of the substrate electrode pad of the substrate.

10. The imaging module according to claim 9, wherein
the electric cable is a coaxial cable and includes an internal conductor and an external conductor,
the substrate has an internal conductor electrode pad provided on the main surface and an external conductor electrode pad provided on the main surface,
the internal conductor electrode pad and the external conductor electrode pad each have a rear end portion,
the internal conductor is connected to the rear end portion of the internal conductor electrode pad,
the external conductor is connected to the rear end portion of the external conductor electrode pad, and
the rear end portion of the internal conductor electrode pad to which the internal conductor of the coaxial cable is connected is positioned on a front side of the rear end portion of the external conductor electrode pad to which the external conductor of the coaxial cable is connected.

11. A method of manufacturing an imaging module comprising:
a preparing step of preparing an imaging element that has an imaging surface and a rear surface opposite to the imaging surface, and includes element electrode pads provided on the rear surface, the element electrode pads having an element solder terminal formed thereon, the element electrode pads extending in a first direction;
a preparing step of preparing a substrate that has a main surface including a substrate electrode pad provided thereon, the substrate having an end face facing the rear surface of the imaging element, the substrate extending in a second direction intersecting with the first direction, the substrate electrode pad having a substrate solder terminal formed thereon, the substrate electrode pad having a front end portion, the front end portion having a notch portion and an end formed by the notch portion, the end being located away from the end face of the substrate, the notch portion being formed at the front end portion of the substrate electrode pad so as to cause the main surface of the substrate to remain at the notch portion such that the main surface located at the front end portion is exposed through the notch portion;
a positioning step of bringing the element solder terminal into contact with the substrate solder terminal so that the substrate is positioned on the rear surface of the imaging element, is disposed in a direction extending from the rear surface to a side opposite to the imaging surface, and is positioned with respect to the imaging element; and
a step of forming a conductive connecting material portion electrically connecting the element electrode pads to the substrate electrode pad, in which the element solder terminal of the imaging element and the substrate solder terminal of the substrate are heat-melted to be integrated and then cooled and solidified while maintaining the positioning state of the substrate with respect to the imaging element in the positioning step; wherein
the substrate solder terminal of the substrate is formed at the front end portion of the substrate electrode pad of the substrate at a position close to the imaging element,
the notch portion is formed at the front end portion of the substrate electrode pad and the substrate solder terminal on the substrate such that the main surface located at the front end portion is exposed through the notch portion and contacts the conductive connecting material portion, and wherein
in the positioning step, the substrate is positioned with respect to the imaging element by bringing the front end portion of the substrate electrode pad and an edge portion of the substrate solder terminal facing the notch portion which are on the substrate into contact with the element solder terminal of the imaging element and bringing the element solder terminal of the imaging element into contact with the main surface which is exposed through the notch portion.

12. The method of manufacturing an imaging module according to claim 11, wherein
in the positioning step, the substrate is positioned with respect to the imaging element by disposing the front end portion of the substrate at a position close to the imaging element between a plurality of element solder terminals provided on the rear surface of the imaging element to be spaced apart from each other and by bringing the front end portion of the substrate electrode pad provided on the main surfaces on both sides and an edge portion of the substrate solder terminal facing the notch portion which are on the substrate into contact with the element solder terminal of the imaging element.

* * * * *